US011103486B2

(12) United States Patent
Powell et al.

(10) Patent No.: US 11,103,486 B2
(45) Date of Patent: Aug. 31, 2021

(54) TREATMENT OF AUTOIMMUNE DISORDERS AND INFECTIONS USING ANTAGONISTS OF SGK1 ACTIVITY

(71) Applicant: THE JOHNS HOPKINS UNIVERSITY, Baltimore, MD (US)

(72) Inventors: Jonathan David Powell, Baltimore, MD (US); Emily Beth Heikamp, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 523 days.

(21) Appl. No.: 15/062,576

(22) Filed: Mar. 7, 2016

(65) Prior Publication Data
US 2017/0027915 A1 Feb. 2, 2017

Related U.S. Application Data

(62) Division of application No. 14/118,261, filed as application No. PCT/US2012/038252 on May 17, 2012.

(60) Provisional application No. 61/487,783, filed on May 19, 2011.

(51) Int. Cl.
A61K 31/437 (2006.01)
A61K 31/4439 (2006.01)
A61K 31/7088 (2006.01)
A61K 31/713 (2006.01)
A61K 38/00 (2006.01)
A61K 38/02 (2006.01)
A61K 39/395 (2006.01)

(52) U.S. Cl.
CPC ........ A61K 31/437 (2013.01); A61K 31/4439 (2013.01); A61K 31/7088 (2013.01); A61K 31/713 (2013.01); A61K 38/005 (2013.01); A61K 38/02 (2013.01); A61K 39/3955 (2013.01)

(58) Field of Classification Search
CPC .............. A61K 31/437; A61K 31/4439; A61K 31/7088
See application file for complete search history.

(56) References Cited

U.S. PATENT DOCUMENTS

| 5,296,353 | A | 3/1994 | Ochoa et al. |
| 5,595,756 | A * | 1/1997 | Bally ................... A61K 9/1272 264/4.1 |
| 6,120,763 | A | 9/2000 | Fakharai et al. |
| 6,407,218 | B1 | 6/2002 | Tamarkin et al. |
| 6,500,641 | B1 | 12/2002 | Chen et al. |
| 6,825,174 | B2 | 11/2004 | Nyce |
| 7,129,222 | B2 | 10/2006 | Nest et al. |
| 7,329,678 | B2 | 2/2008 | Drewry et al. |
| 7,405,239 | B2 | 7/2008 | Gericke et al. |
| 7,619,115 | B2 * | 11/2009 | Gericke ............ C07D 295/135 544/162 |
| 2006/0121465 | A1 | 6/2006 | Lang et al. |
| 2006/0148848 | A1 | 7/2006 | Zhang et al. |
| 2007/0059695 | A1 | 3/2007 | Lang |
| 2008/0226645 | A1 | 9/2008 | O'Toole et al. |
| 2009/0136920 | A1 | 5/2009 | Golz et al. |
| 2009/0233955 | A1 * | 9/2009 | Frazee ..................... A61P 9/00 514/300 |

FOREIGN PATENT DOCUMENTS

| WO | 2004004834 A1 | 1/2004 |
| WO | 2005106491 A2 | 11/2005 |
| WO | 2007121963 A1 | 11/2007 |
| WO | 2009103494 A2 | 8/2009 |

OTHER PUBLICATIONS

Ma. Modern Drug Discovery 2004, 7(6): 30-36 (Year: 2004).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Jain RK. Scientific American, Jul. 1994, 58-65 (Year: 1994).*
Vujanovic et al. Journal of Cellular Biochemistry 102:301-310 (2007). (Year: 2007).*
Delgoffe et al., mTOR: taking cues from the immune microenvironment., (2009) Immunology, 127(4), 459-65.
Powell et al., The Mammalian Target of Rapamycin: Linking T Cell Differentiation, Function, and Metabolism., (2010) Immunity, 33(3), 301-311.
Peter et al., mTor signalling and metabolic regulation of T cell differentiation., (2010) Current Opinion in Immunology, 22(5), 655-661.
Araki et al., The role of mTOR in memory CD* T-cell differentiation., (2010) Immunological Reviews, 235(1), 234-243.
Delgoffe, Kole et al., The mTOR Kinase Differentially Regulates Effector and Regulatory T Cell Lineage Commitment., (2009) Immunity, 30(6), 832-844.
Delgoffe, Pollizzi et al., The kinase mTOR regulates the differentiation of helper T cells through the selective activation of signaling by mTORC1 and mTORC2., (2011) Nature Immunology, 12(4), 295-303.
Garcia-Martinez et al., mTOR complex 2 (mTORC2) controls hydrophobic motif phosphorylation and activation of serum- and glucocorticoid-induced protein kinase 1 (SGK1), (2008) The Biochemical Journal, 416(3), 375-385.

(Continued)

Primary Examiner — Vanessa L. Ford
Assistant Examiner — Sandra E Dillahunt
(74) Attorney, Agent, or Firm — Casimir Jones, S.C.; Melissa E. Karabinis

(57) ABSTRACT

The present invention provides novel methods for treating Th2-mediated immune disorders and enhancing Th1-mediated immune responses in a subject comprising administering to the subject, a pharmaceutical composition comprising a serum-glucocorticoid regulated kinase 1 (SGK1) inhibitor and a pharmaceutically acceptable carrier. Methods for treating a wide range of autoimmune diseases are also taught. The present invention also provides methods for augmenting the treatment of subjects having viral or parasitic infections, or which have cancerous tumors.

4 Claims, 19 Drawing Sheets

Specification includes a Sequence Listing.

(56) References Cited

OTHER PUBLICATIONS

Sarbassov et al., Phosphorylation and Regulation of Akt/PKB by the Rictor-mTOR Complex, (2005) Science, 307 (5712), 1098-1101.
Hresko et al., mTOR-RICTOR Is the Ser473 Kinase for Akt/Protein Kinase B in 3T3-L1 Adipocytes, (2005) The Journal of Biological Chemistry, 280(49).
Holz et al., Identification of S6 Kinase 1 as a Novel Mammalian Target of Rapamycin (mTOR)-phosphorylating Kinase, (2005) Journal of Biological Chemistry, 280:26089-93.
Murray et al., Exploitation of KESTREL to identify NDRG family members as physiological substrates for SGK1 and GSK3., (2004) The Biochemical Journal, 384(3), 477-88.
Debonneville et al., Phosphorylation of Nedd4-2 by Sgk1 regulates epithelial $Na^+$ channel cell surface expression, (2001) The EMBO Journal, 20, 7052-7059.
Wiemuth et al., Interaction of serum- and glucocorticoid regulated kinase 1 (SGK1) with the WW-domains of Nedd4-2 is required for epithelial sodium channel regulation., (2010) PLoS One, 5(8).
Oliver et al., Ndfip1 protein promotes the function of itch ubiquitin ligase to prevent T cell activation and T helper 2 cell-mediated inflammation., (2006) Immunity, 25(6), 929-940.
Li et al., Regulation of IL-4 expression by the transcription factor JunB during T helper cell differentiation., (1999) The EMBO Journal, 18(2), 420-432.
Sakoda et al., Differing Roles of Akt and Serum- and Glucocorticoid-regulated Kinase in Glucose Metabolism, DNA Synthesis, and Oncogenic Activity, (2003) Journal of Biological Chemistry, 278(28).
Yu et al., TCF1 and beta-catenin regulate T cell development and function., (2010) Immunologic Research, 47(1), 45-55.
Gueders et al., Mouse models of asthma: a comparison between C57BL/6 and BALB/c strains regarding bronchial responsiveness, inflammation, and cytokine production., (2009) Inflammation Research: Official Journal of the European Histamine Research Society, 58(12), 845-54.
Araki, Turner et al., mTOR regulates memory CD8 T-cell differentiation., (2009) Nature, 460(7251), 108-112.
Kaech et al., Selective expression of the interleukin 7 receptor identifies effector CD8 T cells that give rise to long-lived memory cells, (2003) Nature Immunology, 4, 1191-1198.
Sarkar et al., Functional and genomic profiling of effector CD8 T cell subsets with distinct memory fates., (2008) The Journal of Experimental Medicine, 205(3), 625-640.
Schluns et al., Interleukin-7 mediates the homeostasis of naïve and memory CD8 T cells in vivo., (2000) Nature Immunology, 1(5), 426-432.
Sallusto et al., From vaccines to memory and back., (2010) Immunity, 33(4), 451-63.
Sobiesiak et al., Impaired Mast Cell Activation in Gene-Targeted Mice Lacking the Serum- and Glucocorticoid-Inducible Kinase SGK1, (2009) Journal of Immunology, 183(7), 4395-4402.
Amato et al., IL-2 signals through Sgk1 and inhibits proliferation and apoptosis in kidney cancer cells., (2007) Journal of Molecular Medicine, 85(7), 707-21.
Lang et al., Colorectal carcinoma cells—regulation of survival and growth by SGK1., (2010) The International Journal of Biochemistry and Cell Biology, 42(10), 1571-5.
Gao et al., Rictor forms a complex with Cullin-1 to promote SGK1 ubiquitination and destruction., (2010) Molecular Cell, 39(5), 797-808.
Rauz et al., Expression and distribution of the serum and glucocorticoid regulated kinase and the epithelial sodium channel subunits in the human cornea. (2003) Experimental Eye Research, 77(1), 101-108.
Rauz, Walker et al., Serum- and glucocorticoid-regulated kinase isoform-1 and epithelial sodium channel subunits in human ocular ciliary epithelium. (2003) Investigative Ophthalmology and Visual Science, 44(4), 1643-51.
Verde et al., Potential markers of heavy training in highly trained distance runners., (1992) British Journal of Sports Medicine, 26(3), 167-175.
Wohlfahrt et al., Ephrin-A1 suppresses Th2 cell activation and provides a regulatory link to lung epithelial cells., (2004) Journal of Immunology, 172(2), 843-50.
Pasquier et al., Identification of FcalphaRI as an inhibitory receptor that controls inflammation: dual role of FcRgamma ITAM., (2005) Immunity, 22(1), 31-42.
MacGlashan et al., Nonspecific desensitization, functional memory, and the characteristics of SHIP phosphorylation following IgE-mediated stimulation of human basophils., (2006) Journal of Immunology, 177(2), 1040-51.
Hama et al., Study for an allergic inflammation model using human lungs and its pharmacological application., (2007) Yakugaku Zasshi, 127(4), 721-7.
Takatsu et al., Interleukin 5 in the link between the innate and acquired immune response. (2009) Advances in Immunology, 101, 191-236.
Searing et al., Decreased serum vitamin D levels in children with asthma are associated with increased corticosteroid use. (2010) Journal of Allergy and Clinical Immunology, 125(5), 995-1000.
Chang et al., A novel phycobiliprotein alleviates allergic airway inflammation by modulating immune responses. (2011) American Journal of Respiratory and Critical Care Medicine, 183(1), 15-25.
Roongapinun et al., A novel phycobiliprotein alleviates allergic airway inflammation by modulating immune responses. (2010) PLoS One, 5(11).
Won et al., Protein kinase SGK1 enhances MEK/ERK complex formation through the phosphorylation of ERK2: implication for the positive regulatory role of SGK1 on the ERK function during liver regeneration., (2009) Journal of Hepatology, 51(1), 67-76.
Kim et al., Genotyping and phylogenetic analysis of bovine viral diarrhea virus isolates from BVDV infected alpacas in North America., (2009) Veterinary Microbiology, 136(3), 209-16.
Aoyama et al., Serum and glucocorticoid-responsive kinase-1 regulates cardiomyocyte survival and hypertrophic response., (2005) Circulation, 111(13), 1652-9.

* cited by examiner

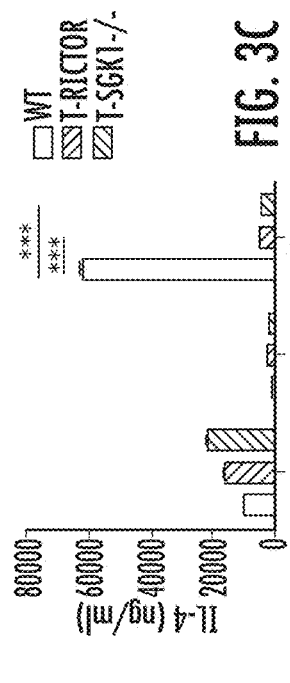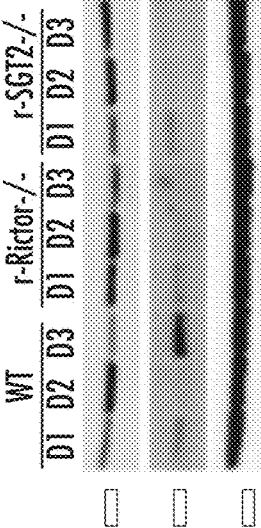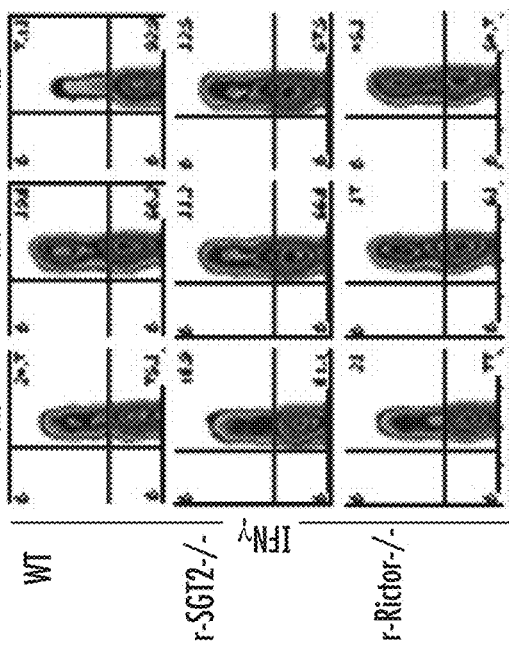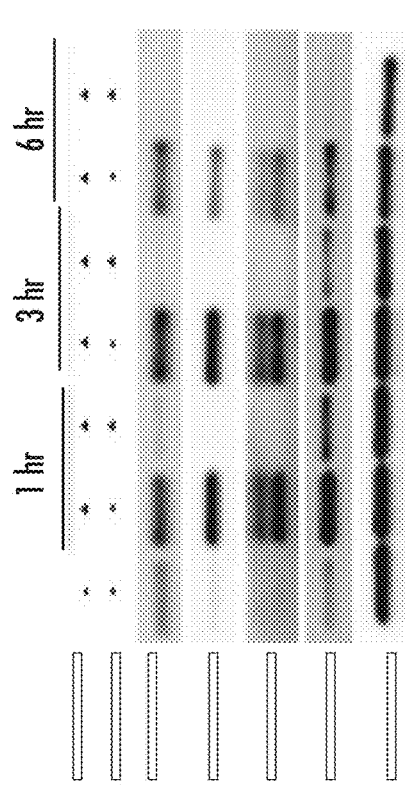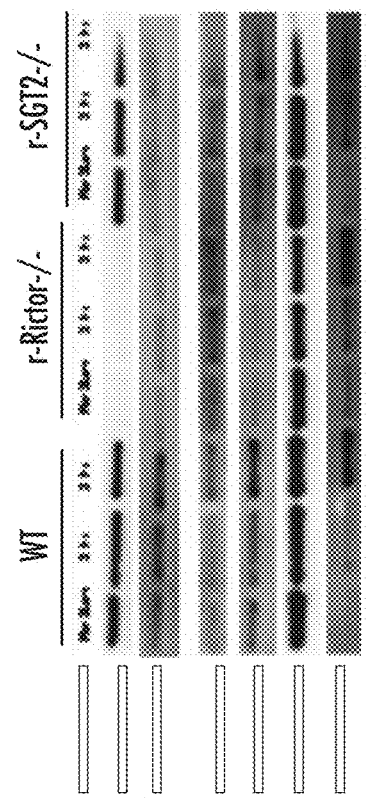
FIG. 3A
FIG. 3B
FIG. 3C
FIG. 3D
FIG. 3E

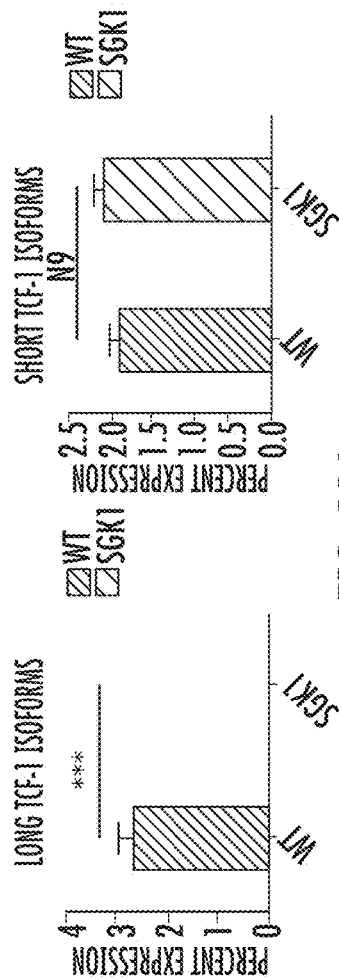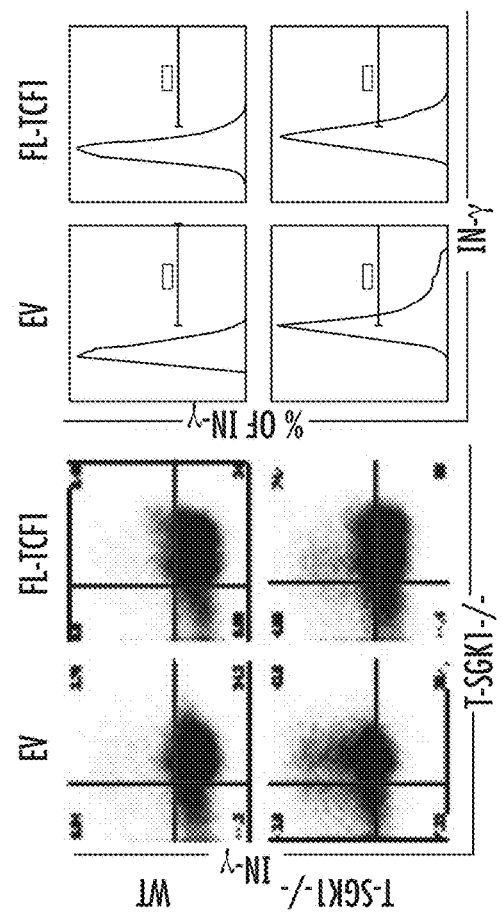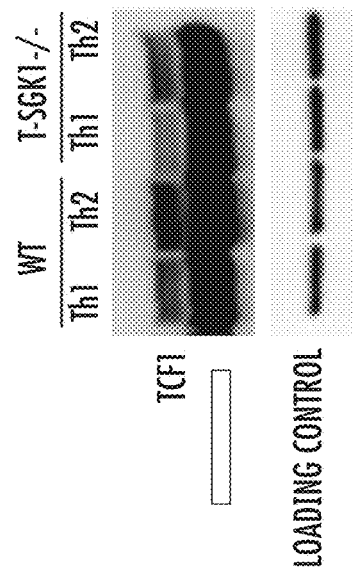
FIG. 11H
FIG. 11I
FIG. 11J
FIG. 11K

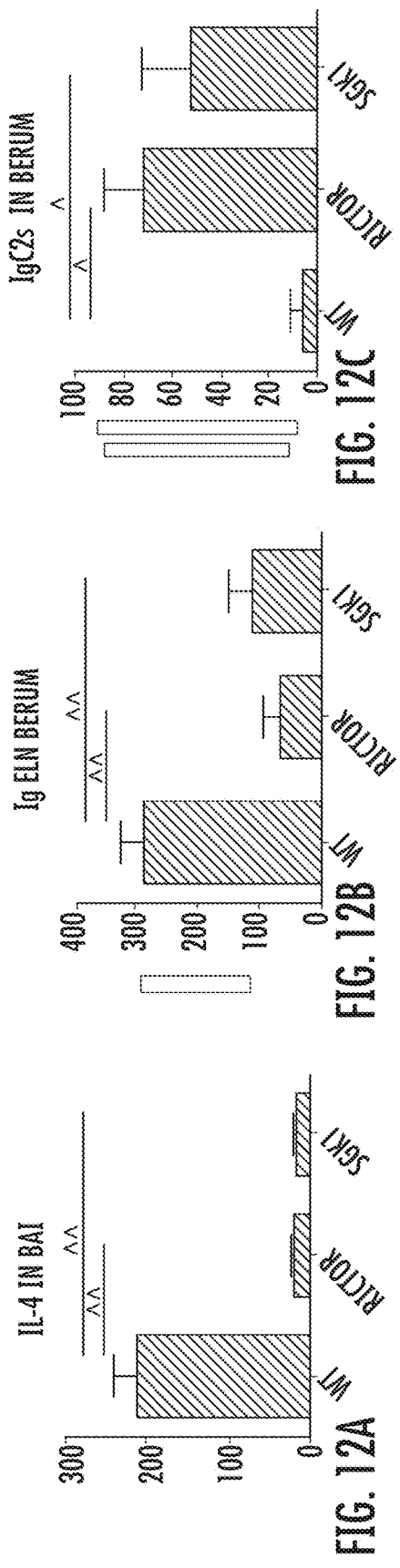
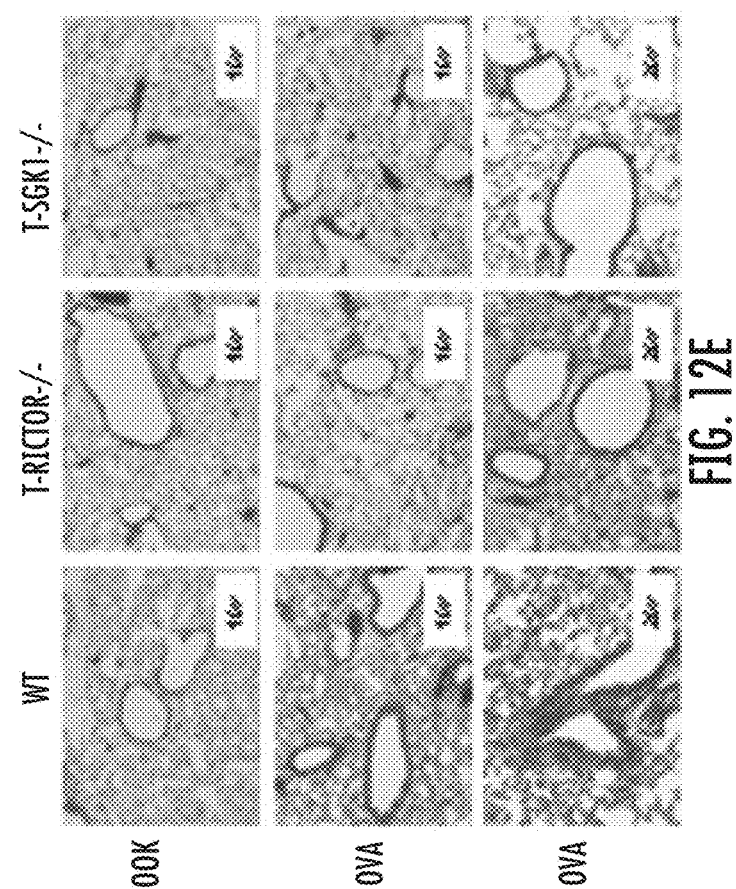
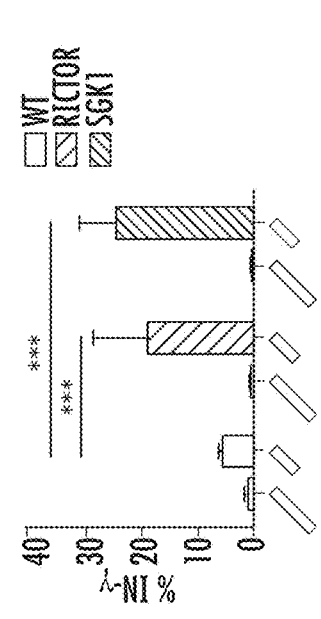
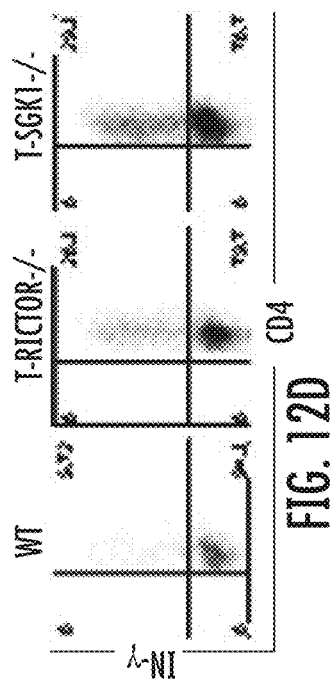
FIG. 12A
FIG. 12B
FIG. 12C
FIG. 12D
FIG. 12E

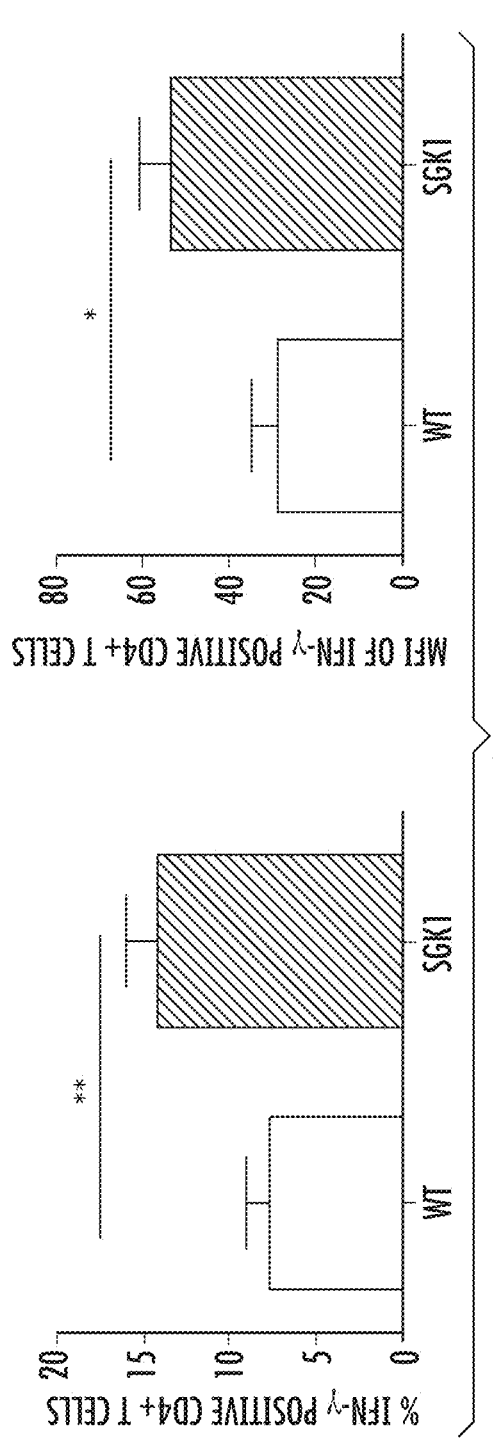
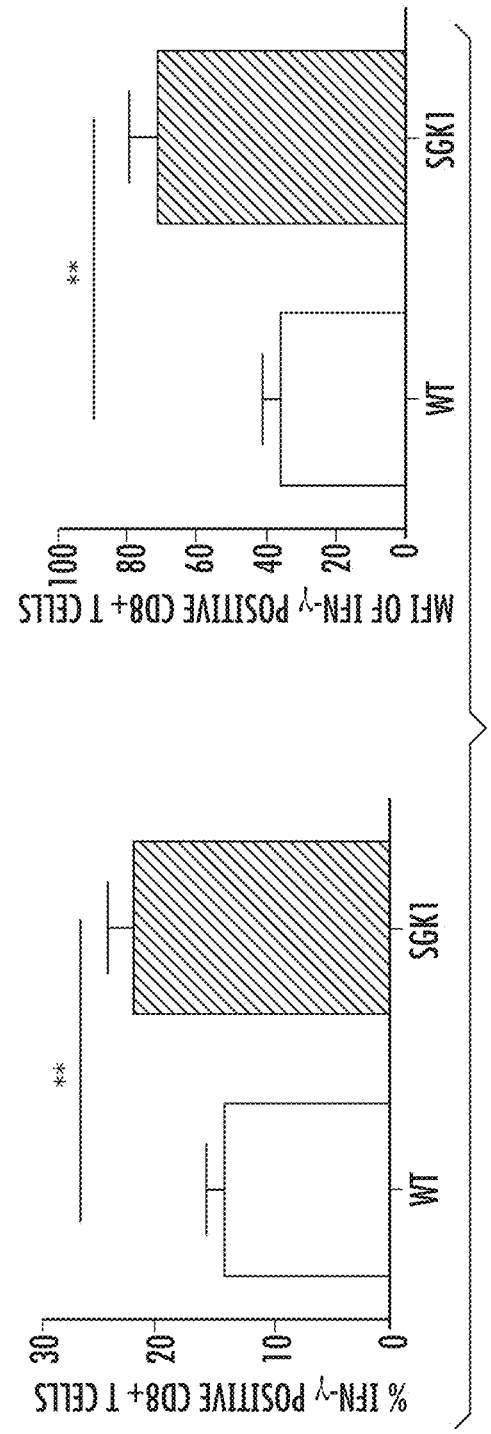
FIG. 13C
FIG. 13D

TREATMENT OF AUTOIMMUNE DISORDERS AND INFECTIONS USING ANTAGONISTS OF SGK1 ACTIVITY

REFERENCE TO RELATED APPLICATIONS

This application is a divisional of U.S. patent application Ser. No. 14/118,261, filed Jan. 13, 2014, which is a 35 U.S.C. § 371 U.S. national entry of International Application PCT/US12/38252 having an international filing date of May 17, 2012, which claims the benefit of U.S. Provisional Application No. 61/487,783 filed May 19, 2011, the content of each of the aforementioned applications is herein incorporated by reference in their entirety.

STATEMENT OF GOVERNMENTAL INTEREST

This invention was made with government support under grant no. AI077610 awarded by the National Institutes of Health. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "P11550-02_ST25". The sequence listing is 587 bytes in size, and was created on May 17, 2012. It is hereby incorporated by reference in its entirety.

BACKGROUND OF THE INVENTION

The mammalian target of rapamycin (mTOR) is an evolutionarily conserved serine-threonine kinase that integrates multiple environmental signals to regulate cell metabolism, proliferation, and survival. In the immune system, mTOR is emerging as a critical integrator of signals from the immune microenvironment leading to T helper cell differentiation and function, APC differentiation and function, and CD8+ T cell memory and effector generation. Our laboratory has shown that mTOR can associate with two distinct protein complexes (mTORC1 and mTORC2) to drive the selective differentiation of CD4+ T cells. Through genetic deletion of various components of the mTOR pathway, we have demonstrated that loss of either mTORC1 or mTORC2 can lead to the differentiation of distinct T effector (Teff) subsets, such as T helper 1 (Th1) and T helper 2 (Th2) cells. While Th1 cells secrete IFNγ and promote cell-mediated immunity, Th2 cells classically make interleukin-4 (IL4) and promote humoral immunity. We have shown that mice lacking mTORC2 through genetic deletion of Rictor in CD4+ T cells (T-Rictor−/−) fail to mount Th2-mediated immune responses, but Th1 differentiation remains intact.

Despite the critical role of mTOR in regulating T cell differentiation, virtually nothing is known about the downstream signaling pathways that control differentiation into these helper T cell subsets.

Immunosuppressive drugs such as steroids, cyclosporine, FK506, cytotoxic agents such Imuran, Cytoxan, and Mycophenolate mofetil, all non-specifically inhibit the immune system. As such, patients being treated for autoimmune disease or cancer or who have received organ transplants are susceptible to infections. There exists therefore, an unmet need to develop therapeutics which can suppress the autoimmune symptoms but allow subjects to continue to fight infection.

SUMMARY OF THE INVENTION

In accordance with an embodiment, the present invention provides a method for treating a Th2-mediated immune disorder in a subject comprising administering to the subject, a pharmaceutical composition comprising a serum-glucocorticoid regulated kinase 1 (SGK1) inhibitor and a pharmaceutically acceptable carrier, in an effective amount such that the Th2-mediated immune response in the subject is diminished when compared to a non-treated subject.

In accordance with another embodiment, the present invention provides a method for enhancing a Th1-mediated immune response in a subject comprising administering to the subject, a pharmaceutical composition comprising a serum-glucocorticoid regulated kinase 1 (SGK1) inhibitor and a pharmaceutically acceptable carrier, in an effective amount such that the Th1-mediated immune response in the subject is increased when compared to a non-treated subject.

In accordance with a further embodiment, the present invention provides a method for treating an autoimmune disease in a subject comprising administering to the subject, a pharmaceutical composition comprising a serum-glucocorticoid regulated kinase 1 (SGK1) inhibitor and a pharmaceutically acceptable carrier, in an effective amount such that the symptoms of the disease in the subject are diminished.

In accordance with still another embodiment, the present invention provides a method for treating a viral infection, a parasitic infection or a tumor in a subject comprising administering to the subject, a pharmaceutical composition comprising a serum-glucocorticoid regulated kinase 1 (SGK1) inhibitor and a pharmaceutically acceptable carrier, in an effective amount such that the symptoms of the infection or tumor in the subject are diminished.

In accordance with an embodiment, the present invention provides a method for enhancing the immune response in a subject receiving a vaccine comprising administering to the subject, an effective amount of a pharmaceutical composition comprising a serum-glucocorticoid regulated kinase 1 (SGK1) inhibitor and a pharmaceutically acceptable carrier, and then subsequently administering to the subject, an effective amount of a vaccine.

BRIEF DESCRIPTION OF THE DRAWINGS

FIG. 3A-3E depict that SGK1 promotes Th2 differentiation, but negatively regulates Th1 differentiation. (3A) Immunoblot (IB) of Wt, T-Rictor−/−, and T-SGK1−/− CD4+ T cells. Cells were serum starved for 1 hour prior to stimulation with anti-CD3 and anti-CD28. Cells were lysed, and the activity of mTORC1 and mTORC2 was measured by blotting for S6 (S240/244) and S6 Kinase (T389) activity downstream of TORC1, and for Akt activity upstream of TORC1 (T308) and downstream of TORC2 (S473). To measure the activity of downstream targets of Akt and SGK1, cells were blotted for Foxo1 (Thr24)/Foxo3a (Thr32), and for NDRG1 (T346). Pan Akt and total S6 are included as loading controls. (3B) IFN-γ production of activated CD4+ T cells by intracellular staining. Naïve $CD4^{+P}$ T cells from Wt, T-Rictor$^{-/-}$, and T-SGK1-/- mice were isolated based on expression of CD44 and CD62L (data not shown). Cells were stimulated with irradiated autologous APCs, 1 mg/mL anti-CD3, and either (Th0) IL-2 or (Th1) IL-12, IFN-γ, and anti-IL-4, or (Th2) IL-4, anti-IFN-γ, and anti-IL-12p40 skewing conditions for 2 days. After stimulation, cells were rested in IL-2 prior to restimulation overnight with anti-CD3 and anti-CD28 in the presence of a protein transport inhibitor. Cells were fixed, permeabilized, and stained for IFN-γ intracellularly. (3C) IL-4 production of activated CD4+ T cells by ELISA. As in B, but in the absence of protein transport inhibitor during restimulation. (3D) Expression of Tbet by intracellular staining. As in B, but in the absence of protein transport inhibitor during restimulation. (3E) IB of activated CD4+ T cells for lineage-specific transcription factors. As in B, but in the absence of protein transport inhibitor during restimulation. Cells were lysed and immunoblotted for Tbet and GATA3. Actin is included as a loading control.

FIG. 11A-11K show that SGK1 regulates JunB and TCF-1 to influence helper T cell differentiation. (11A) Nuclear and cytoplasmic extracts from Wt and T-SGK1-/- CD4+ T cells. Cells were purified by magnetic separation and stimulated for 72 hours in vitro with anti-CD3 and anti-CD28 and either (Th1) IL-12, IFN-γ, and anti-IL-4, or (Th2) IL-4, anti-IFN-γ, and anti-IL-12p40 skewing conditions. Cells were lysed and separated into nuclear and cytoplasmic fractions. Nuclear extracts were blotted for the expression of JunB, and Lamin B is included as a loading control. Cytosolic fractions were blotted to measure the E3 ligase activity of NEDD4L (S342), and actin is included as a loading control. (11B) Nuclear extract of Wt and T-SGK1-/- treated with MG132. As in A, but with the addition of the proteasome inhibitor MG-132 during the final 2 hours of stimulation. Nuclear fractions were blotted for JunB. (11C) Immunoprecipitates (IPs) of JunB from Wt and T-SGK1-/- CD4+ T cells skewed with IL4 and treated with MG132. As in B, but nuclear fractions were subject to IP with JunB antibody. Bar graphs representing the raw spectrophotometric analysis of the immunoblots of JunB (11D) and NEDD4L (11E) and their normalized data (11F, 11G) respectively. IPs were blotted for ubiquitin, NEDD4L, and JunB is included as a loading control. (11H) Nuclear and cytoplasmic extracts from Wt and T-SGK1-/- CD4+ T cells. As in A, but lysates were blotted for TCF1 (Clone C63D9) and activity of β-Catenin (S33, 37, T41). (11I) Representation of long and short isoforms of TCF1 with location of primer binding sites to detect long and short transcripts. (11J) Expression of long and short isoforms of TCF-1 in activated CD4+ T cells. CD4+ T cells were purified from Wt and T-SGK1-/- mice by magnetic separation, stimulated with irradiated autologous APCs and 1 μg/mL anti-CD3 for 2 days, and rested in rested in IL-2 prior to restimulation overnight with anti-CD3 and anti-CD28. Fold induction of long and short isoforms of TCF1 over no stimulation control, as analyzed by quantitative polymerase chain reaction. (11K) Flow cytometric analysis of CD4+ T cells overexpressing TCF1. CD4+ T cells were purified from Wt and T-SGK1-/- mice by magnetic separation and stimulated overnight with 3 μg/mL anti-CD3 and anti-CD28 under Th2 skewing conditions. During the next 24 hours of stimulation, cells were incubated with MSCV-based retrovirus expressing the long isoform of TCF1 and a human CD8 marker. Following transduction, cells were rested in IL-2 for 5 days then sorted for human CD8 surface expression. Cells were restimulated for 4 hours with phorbol 12-myristate 13-acetate (PMA) and ionomycin in the presence of a protein transport inhibitor, and analyzed for production of IFN-γ by intracellular staining.

FIG. 12A-12E depict that the loss of TORC2 activity in CD4+ T cells abolished signs of Th2-mediated disease in an asthma model. (12A) IL-4 production in bronchoalveolar lavage (BAL). Wt, T-Rictor-/- and T-SGK1-/- mice were immunized intraperitoneally with ovalbumin (OVA) protein and aluminum hydroxide on day 0 and boosted via the same protocol on day 7. On days 15, 16, and 17, mice were challenged with intranasal injections of OVA, and mice were harvested on day 18. Lungs were lavaged with PBS and analyzed by ELISA for the presence of IL-4. (12B) OVA-specific IgG1 in serum. As in A, but serum was analyzed by ELISA for the presence of the antigen-specific Th2 isotype IgG1. (12C) OVA-specific IgG2a in serum. As in A, but serum was analyzed by ELISA for the presence of the antigen-specific Th1 isotype IgG2a. (12D) IFN-γ production by lung lymphocytes. As in A, lung lymphocytes were harvested from diseased mice and stimulated for 4 hours in vitro with phorbol 12-myristate 13-acetate (PMA) and ionomycin in the presence of a protein transport inhibitor, and analyzed for production of IFN-γ by intracellular staining. (12E) Representative lung sections after H&E staining are shown for saline control (mock) and OVA sensitized/OVA aerosol challenged Wt, T-Rictor−/− and T-SGK1−/− mice. Pathologic changes in Wt mice include lymphocytic infiltration and epithelial hyperplasia.

FIG. 13A-13D show that the loss of SGK1 enhances CD4+ and CD8+ mediated tumor immunity. (13A) Number of B16-melanoma lung metastases. Wt and T-SGK1−/− mice were injected intravenously with 500,000 B16 melanoma cells, and lungs were harvested 21 days later. The number of lung metastases were counted and expressed as mean+SD. (13B) As in A, lungs were weighed and mass is expressed in mg. (13C) As in A, lung lymphocytes were harvested and stimulated for 4 hours in vitro with PMA and ionomycin in the presence of a protein transport inhibitor, and analyzed by intracellular staining for production of IFN-γ by CD4+ T cells. (13D) As in B, but lung lymphocytes were analyzed intracellular staining for production of IFN-γ by CD8+ T cells. Representative images from one of three experiments showing reduced tumor burden in the lungs of Wt mice compared to T-SGK1−/− mice.

DETAILED DESCRIPTION OF THE INVENTION

Figure 1:
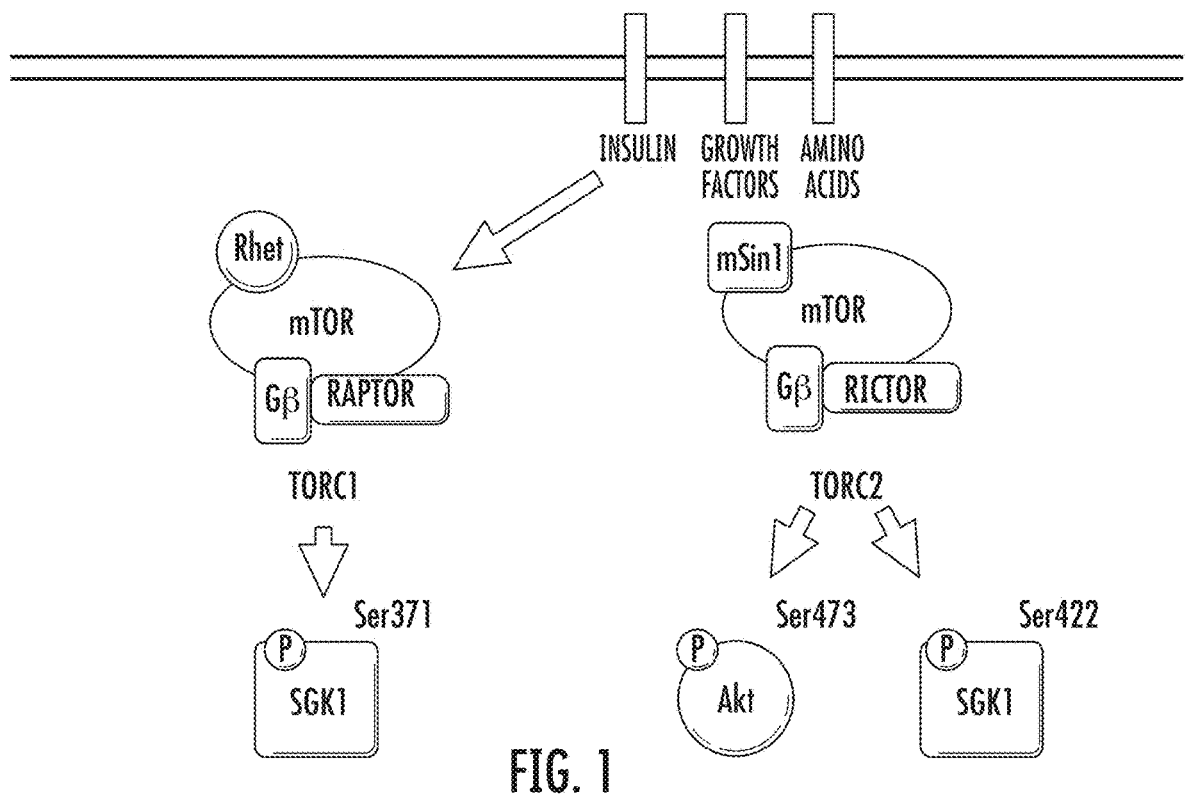
FIG. 1 depicts a schematic showing that SGK1 is a downstream target of TORC2.

In accordance with one or more embodiments, the inventors demonstrate that SGK1 selectively and reciprocally regulates helper T cell differentiation downstream of mTORC2. As a result, it is understood that targeting SGK1 is beneficial in the setting of autoimmune diseases that are mediated by Th2 immune responses, such as in the setting of allergic asthma. Conversely, inhibiting SGK1 is useful in diseases in which a Th1 response is therapeutic, such as in the treatment of cancer and tumors. By defining SGK1 as a downstream node in the mTOR signaling network, the methods of the present invention provide further insight into how this pathway regulates T cell differentiation in physiologic settings, in addition to how this pathway can be manipulated in pathologic settings to achieve a productive immune response (FIG. 1).

In accordance with an embodiment, the present invention provides a method for treating a Th2-mediated immune disorder in a subject comprising administering to the subject, a pharmaceutical composition comprising a SGK1 inhibitor and a pharmaceutically acceptable carrier, in an effective amount such that the Th2-mediated immune response in the subject is diminished when compared to a non-treated subject.

It will be understood that the term SGK1 inhibitor, as used herein, means any compound which when in the presence of the SGK1 enzyme, inhibits the function of the enzyme, either in vitro, or in vivo. Examples of classes of SGK1 inhibitor useful in the methods of the present invention include, for example, antibodies, oligonucleotides such as siRNA or microRNA, small molecules, peptides and derivatives thereof.

The antibodies, or functional fragments thereof, used with the methods of the present invention, can be monoclonal or polyclonal, and can include IgA, IgG, IgE, and should have sufficient specificity to bind to the SGK1 enzyme so as to inhibit the binding of the endogenous substrate to the enzyme. The peptides of the invention can be a recombinant antibody. As used herein, "recombinant antibody" refers to a recombinant (e.g., genetically engineered) protein comprising a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. The polypeptide of an antibody, or portion thereof, can be a polypeptide of any antibody or any antibody fragment, including any of the antibodies and antibody fragments described herein.

The term "polynucleotide," as used herein, includes and/or is synonymous with "nucleic acid," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

The term "polyribonucleotide," as used herein, includes "ribonucleic acid," "oligoribonucleotide," and "ribonucleic acid molecule," and generally means a polymer of RNA which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It may be suitable in some instances, in an embodiment, for the nucleic acids to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The present invention also relates to compounds, compositions, and methods useful for modulating the expression and activity of a target gene of interest, or expression and/or activity by RNAi using small nucleic acid molecules. As used herein, the instant invention features small nucleic acid molecules, or polyribonucleotides, and includes terms such as such as siRNA, siNA, dsRNA, miRNA, and shRNA molecules and methods used to modulate the expression of target genes of interest.

A polyribonucleotide of the invention can be unmodified or chemically modified. A polyribonucleotide of the instant invention can be chemically synthesized, expressed from a vector or enzymatically synthesized. The instant invention also features various chemically modified polyribonucleotides, including, for example, siRNA molecules capable of modulating repeat expansion gene expression or activity in cells by RNAi. The use of chemically modified siRNA improves various properties of native siRNA molecules through increased resistance to nuclease degradation in vivo and/or through improved cellular uptake.

In one embodiment, the polyribonucleotide molecule of the present invention comprises modified nucleotides while maintaining the ability to mediate RNAi. The modified nucleotides can be used to improve in vitro or in vivo characteristics, such as stability, activity, and/or bioavailability. For example, when the polyribonucleotide molecule is a siRNA molecule, the invention can comprise modified nucleotides as a percentage of the total number of nucleotides present in the siRNA molecule. As such, an siRNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siRNA molecule will depend on the total number of nucleotides present in the siRNA. If the siRNA molecule is single-stranded, the percent modification can be based upon the total number of nucleotides present in the single-stranded siRNA molecules. Likewise, if the siRNA molecule is double-stranded, the percent modification can be based upon the total number of nucleotides present in the sense strand, antisense strand, or both the sense and antisense strands.

The term "modulate," as used herein means that the expression of the target gene, or level of RNA molecule or equivalent RNA molecules encoding one or more target proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

The terms "inhibit," "down-regulate," "reduce," or "knockdown," as used herein, means that the expression of the target gene, or level of RNA molecules or equivalent RNA molecules encoding one or more target proteins or protein subunits, or activity of one or more target proteins or protein subunits, is reduced below that observed in the absence of the polyribonucleotide molecules (e.g., siRNA) of the invention. In an embodiment, inhibition, down-regulation or reduction with a siRNA molecule is below that level observed in the presence of an inactive or attenuated molecule. In another embodiment, inhibition, down-regulation, or reduction with siRNA molecules is below that level observed in the presence of, for example, a siRNA molecule with scrambled sequence or with mismatches. In another embodiment, inhibition, down-regulation, or reduction of target gene expression with a nucleic acid molecule of the instant invention is greater in the presence of the nucleic acid molecule than in its absence.

By "gene", or "target gene", is meant, a nucleic acid that encodes a RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), miRNA, small nuclear RNA (snRNA), siRNA, small nucleolar RNA (snRNA), ribosomal RNA (rRNA), transfer RNA (tRNA) and precursor RNAs thereof. Such non-coding RNAs can serve as target nucleic acid molecules for siRNA mediated RNA interference in modulating the activity of fRNA or ncRNA involved in functional or regulatory cellular processes. Aberrant fRNA or ncRNA activity leading to disease can therefore be modulated by polyribonucleotide molecules of the invention. Polyribonucleotide molecules targeting fRNA and ncRNA can also be used to manipulate or alter the genotype or phenotype of an organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof.

The length of the siRNA molecule can be any length greater than about 10 bp, which is capable of binding its complementary sequence on the mRNA of the target gene of interest in the cytosol of a cell or population of cells. The length of the siRNA can be about 20 to about 50 bp, including, for example, 20 bp, 25 bp, 30 bp, 35 bp, 40 bp, 45 bp, up to and including 50 bp.

In accordance with an embodiment, the methods of the present invention include inhibition of SGK1 activity by the administration of pharmaceutical compositions comprising one or more small molecules. Examples of small molecule inhibitors of SGK1 activity can be found in U.S. Pat. Nos. 7,329,678, 7,619,115, and 7,405,239, and U.S. Patent Publication No. 2009/0233955, and which are incorporated by references in their entirety.

In accordance with an embodiment, the present invention provides a method for treating a Th2-mediated immune disorder in a subject comprising administering to the subject, a pharmaceutical composition comprising 2-cyclopentyl-4-(5-phenyl-1H-pyrrolo[2,3b]pyridine-3yl)-benzoic acid (1) and a pharmaceutically acceptable carrier, in an effective amount such that the Th2-mediated immune response in the subject is diminished when compared to a non-treated subject.

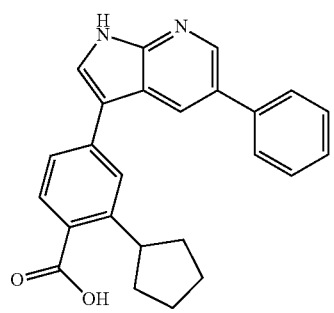

(1)

In accordance with another embodiment, the present invention provides a method for treating a Th2-mediated immune disorder in a subject comprising administering to the subject, a pharmaceutical composition comprising 2-cyclopentyl-4-(5-phenyl-1H-pyrrolo[2,3b]pyridine-3yl)-benzoic acid (1), at least one additional therapeutic agent, and a pharmaceutically acceptable carrier, in an effective amount such that the Th2-mediated immune response in the subject is diminished when compared to a non-treated subject.

In accordance with a further embodiment, the present invention provides a method for enhance a Th1-mediated immune response in a subject comprising administering to the subject, a pharmaceutical composition comprising 2-cyclopentyl-4-(5-phenyl-1H-pyrrolo[2,3b]pyridine-3yl)-benzoic acid (1) and a pharmaceutically acceptable carrier, in an effective amount such that the Th1-mediated immune response in the subject is increased when compared to a non-treated subject.

In accordance with still another embodiment, the present invention provides a method for enhance a Th1-mediated immune response in a subject comprising administering to the subject, a pharmaceutical composition comprising 2-cyclopentyl-4-(5-phenyl-1H-pyrrolo[2,3b]pyridine-3yl)-benzoic acid (1), at least one additional therapeutic agent, and a pharmaceutically acceptable carrier, in an effective amount such that the Th1-mediated immune response in the subject is increased when compared to a non-treated subject.

As used herein, the term "Th1-mediated immune response" means a cell mediated immune response typically invoked when the subject is challenged by an infection of the subject by a virus, a parasite or due to the presence of cancer in the subject.

It is understood by those of skill in the art, that the term "autoimmune disease" includes diseases which are the result of, in part, of the Th2-mediated immune system of the host. The autoimmune diseases which can be treated by the methods of the present invention include acute disseminated encephalomyelitis, Addison's disease, Allergies, Alopecia areata, Ankylosing Spondylitis, Antiphospholipid syndrome, Asthma, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Cancer, Celiac disease, Chagas disease, Chronic inflammatory demyelinating polyneuropathy, Chronic recurrent multifocal osteomyelitis, Chronic obstructive pulmonary disease, Cold agglutinin disease, Crohn's disease (one of two types of idiopathic inflammatory bowel disease "IBD"), Dermatitis herpetiformis, Dermatomyositis, Diabetes mellitus type 1, Diffuse cutaneous systemic sclerosis, Drug-induced lupus, Discoid lupus erythematosus, Eczema, Endometriosis, Enthesitis-related arthritis, Eosinophilic fasciitis, Gastrointestinal pemphigoid, Glomerulonephritis, Goodpasture's syndrome, Graves' disease, Guillain-Barré syndrome (GBS), Hashimoto's encephalopathy, Hashimoto's thyroiditis, Idiopathic thrombocytopenic purpura (See Autoimmune thrombocytopenic purpura), Interstitial cystitis Juvenile idiopathic arthritis aka Juvenile rheumatoid arthritis, Kawasaki's disease, Lupus erythematosus, Miller-Fisher syndrome, Mixed connective tissue disease, Morphea, Mucha-Habermann disease aka *Pityriasis_lichenoides_et_varioliformis_acuta*, Multiple sclerosis, Myasthenia gravis, Myositis, Narcolepsy, Neuromyelitis optica (also Devic's disease), Neuromyotonia, Occular cicatricial pemphigoid, Opsoclonus myoclonus syndrome, PANDAS (pediatric autoimmune neuropsychiatric disorders associated with *streptococcus*), Paraneoplastic cerebellar degeneration, Paroxysmal nocturnal hemoglobinuria (PNH), Pemphigus vulgaris, Pernicious anaemia, Perivenous encephalomyelitis, Polymyositis, Primary biliary cirrhosis, Primary sclerosing cholangitis, Progressive inflammatory neuropathy, Psoriasis, Psoriatic arthritis, Raynaud phenomenon, Relapsing polychondritis, Reiter's syndrome, Restless leg syndrome, Retroperitoneal fibrosis, Rheumatoid arthritis, Rheumatic fever, Sarcoidosis, Scleroderma, Serum Sickness, Sjögren's syndrome, Spondyloarthropathy, Still's disease, Stiff person syndrome, Transverse myelitis, Ulcerative colitis (one of two types of idiopathic inflammatory bowel disease "IBD"), Undifferentiated connective tissue disease, Urticarial vasculitis, Vasculitis, Vitiligo, and Wegener's granulomatosis In certain embodiments, the autoimmune disease is selected from a group consisting of inflammatory bowel disease (e.g., ulcerative colitis or Crohn's disease), rheumatoid arthritis, diabetes mellitus, celiac disease, autoimmune thyroid disease, autoimmune liver disease, Addison's Disease, Sjögren's Syndrome, transplant rejection, graft vs. host disease and host vs. graft disease. In certain embodiments, the autoimmune disease is a neurological autoimmune disease, such as multiple sclerosis.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzalkonium chloride, benzyl benzoate, cyclodextrins, sorbitan esters, stearic acids), antioxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

In an embodiment, the term "administering" means that the compounds of the present invention are introduced into a subject, preferably a subject receiving treatment for a proliferative disease, and the compounds are allowed to come in contact with the one or more disease related cells or population of cells in vivo.

As defined herein, in another embodiment, the term "contacting" means that the one or more compounds of the present invention are introduced into a sample having at least one cancer cell and appropriate enzymes or reagents, in a test tube, flask, tissue culture, chip, array, plate, microplate, capillary, or the like, and incubated at a temperature and time sufficient to permit binding and uptake of the at least one compound to the cancer cell. Methods for contacting the samples with the compounds, and other specific binding components are known to those skilled in the art, and may be selected depending on the type of assay protocol to be run. Incubation methods are also standard and are known to those skilled in the art.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat an autoimmune disease. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In accordance with one or more embodiments, the methods of the present invention include administering to the subject a pharmaceutical composition comprising at least one other therapeutic agent, either before, concomitant with, or subsequent to administration of the pharmaceutical compositions comprising the SGK1 inhibitor to the subject.

Typically, an attending physician will decide the dosage of the composition with which to treat each individual subject, taking into consideration a variety of factors, such as age, body weight, general health, diet, sex, compound to be administered, route of administration, and the severity of the condition being treated. By way of example, and not intending to limit the invention, the dose of the compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the compositions of the present invention can be at a concentration from about 1 nM to about 100 mM, preferably from about 10 μM to about 50 mM, more preferably from about 100 μM to about 5 mM.

In accordance with an embodiment, the present invention provides a method for enhancing the immune response in a subject receiving a vaccine comprising administering to the subject, an effective amount of a pharmaceutical composition comprising a SGK1 inhibitor and a pharmaceutically acceptable carrier, and then concurrently administering to the subject, an effective amount of a vaccine. In addition, the SGK1 inhibitor can also be administered post-vaccination. In an embodiment, the SGK1 inhibitor is administered about 1 day to about 10 days post-vaccination to further drive a productive Th1-driven immune response.

It will be understood that the type of vaccine administered will be one that induces a Th1-mediated immune response in the subject. Typical examples of such vaccines are those directed to viruses, parasites and tumor antigens.

EXAMPLES

Despite the critical role of mTOR in regulating Teff and Treg differentiation, virtually nothing is known about the downstream signaling pathways that control differentiation into these helper T cell subsets. Several downstream targets of TORC1 and TORC2 have been defined previously. For example, S6 kinase is activated downstream of TORC1, while Akt and SGK1 are activated downstream of TORC2. However, it is unclear how these downstream mediators selectively influence Th1 or Th2 differentiation. While the role of Akt in regulating cell survival and trafficking in CD8+ T cells has recently become appreciated, nothing is known about SGK1 in T cells. Like Akt, SGK1 is an AGC kinase that is phosphorylated by mTORC2 at serine 422 in its hydrophobic motif, and by PDK1 at threonine 256 in its T-loop domain.

Example 1

Figure 2A:
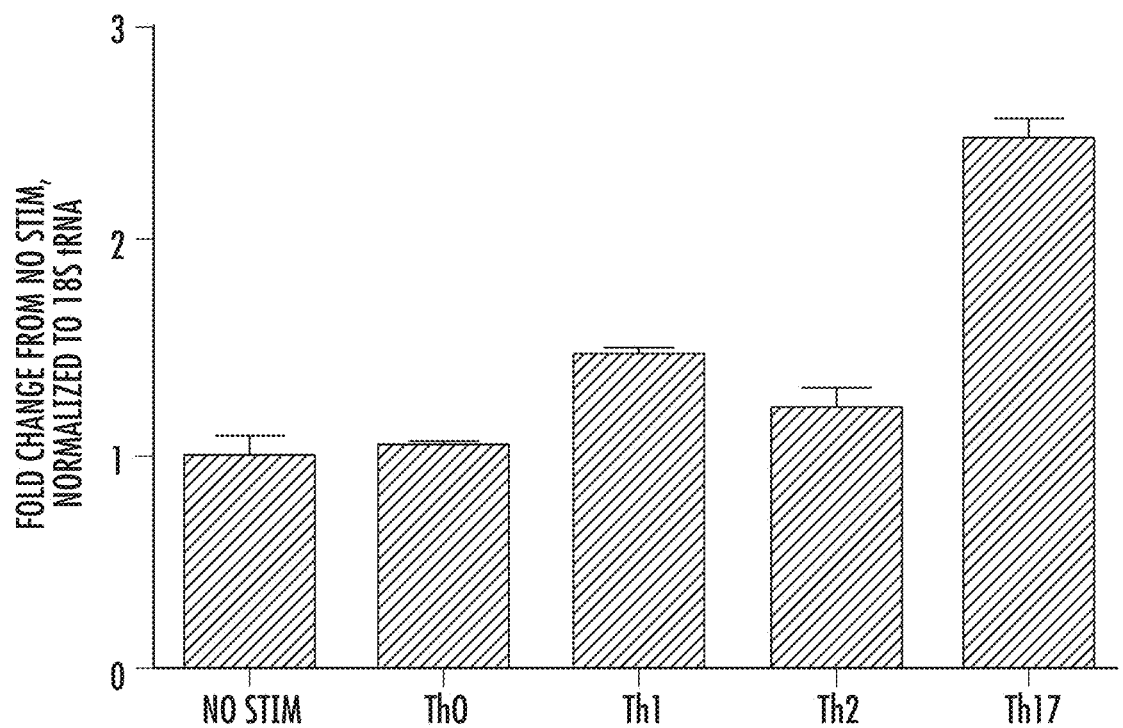
FIG. 2A-2B show that SGK1 mRNA is not expressed in CD4+ or CD8+ T cells from T-SGK1−/− mice, in which SGK1 is specifically deleted in T cells using the Cre-LoxP system under the CD4+ promoter. CD4+ and CD8+ T cells were isolated from Wt and T-SGK1−/− mice by magnetic separation, and mRNA was isolated. (2A) SGK1 mRNA levels were determined by quantitative polymerase chain reaction using the forward primer 5-CTCAGTCTCTTTTGGGCTCTTT-3 (SEQ ID NO: 1) and the reverse primer 5-TTTCTTCTTCAG-GATGGCTTTC-3 (SEQ ID NO: 2), as previously described. (2B) is an exemplary immunoblot showing mRNA expression of SGK1 with GAPDH included as a loading control.
Figure 2B:
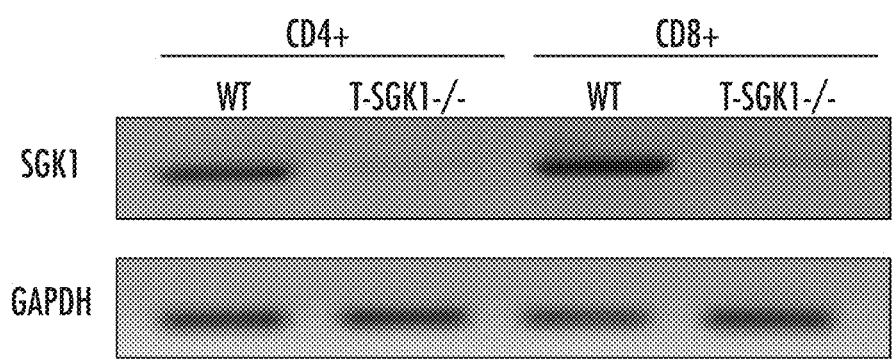

In an effort to determine the mechanism by which mTOR regulates T cell fate, mice were generated in which SGK1 was selectively deleted in T cells. SGK1 foxed mice (A. Fejes-Toth) were bred to CD4-Cre mice, leading to the deletion of SGK1 in T cells, hereafter referred to as T-SGK1−/− mice (FIG. 2). Naïve T cells from Wt, T-Rictor−/− and T-SGK1$^{−/−}$ mice were stimulated with anti-CD3 anti-CD28 and immunoblotted to assay for activity of TORC1 and TORC2 substrates upon TCR engagement (FIG. 3A). Upon stimulation, Wt CD4+ T cells display enhanced mTORC2 activity, as measured by phosphorylation of Akt at serine 473. A selective defect in Akt S473 phosphorylation was observed in T-Rictor−/− mice, which completely lack mTORC2 activity, but this decrease in Akt activity was not observed in T-SGK1−/− mice, indicating that SGK1 functions in a pathway that is downstream of TORC2, yet parallel to Akt. It was previously shown by the inventors that loss of mTORC2 promotes hyperactivation of mTORC1 in CD4+ T cells, as measured by phosphorylation of S6 Kinase and its downstream target S6.

Upon stimulation, Wt T cells show increased phosphorylation of S6 Kinase and S6, but this activation was enhanced in both T-Rictor−/− and T-SGK1−/−. These results are consistent with previous reports that mTORC2 provides some negative feedback on mTORC1 activity, and the present data suggests that this mechanism occurs via activation of SGK1. Although it has been reported that SGK1 phosphorylates FKHRL1/Foxo3a at threonine 32 in 293 cells, the phosphorylation of both Foxo3a and Foxo 1 was unaffected in T-SGK1−/− CD4+ T cells. Interestingly, a selective defect in phosphorylation of Foxo1 at threonine 24 was also observed in T-Rictor−/− CD4+ T cells, indicating that Akt (or perhaps another kinase downstream of TORC2) is responsible for regulating this transcription factor in T cells. While Akt and SGK1 both regulate the phosphorylation of Foxo proteins, another downstream target that is exclusive to SGK1 is the N-myc down-stream-regulated gene-1 (NDRG1). In Wt T cells, it was observed that NDRG1 is phosphorylated at threonine 346 upon T cell activation, but activation of NDRG1 was not observed in both T-Rictor−/− and T-SGK1−/− CD4+ T cells.

Example 2

Figure 4B:
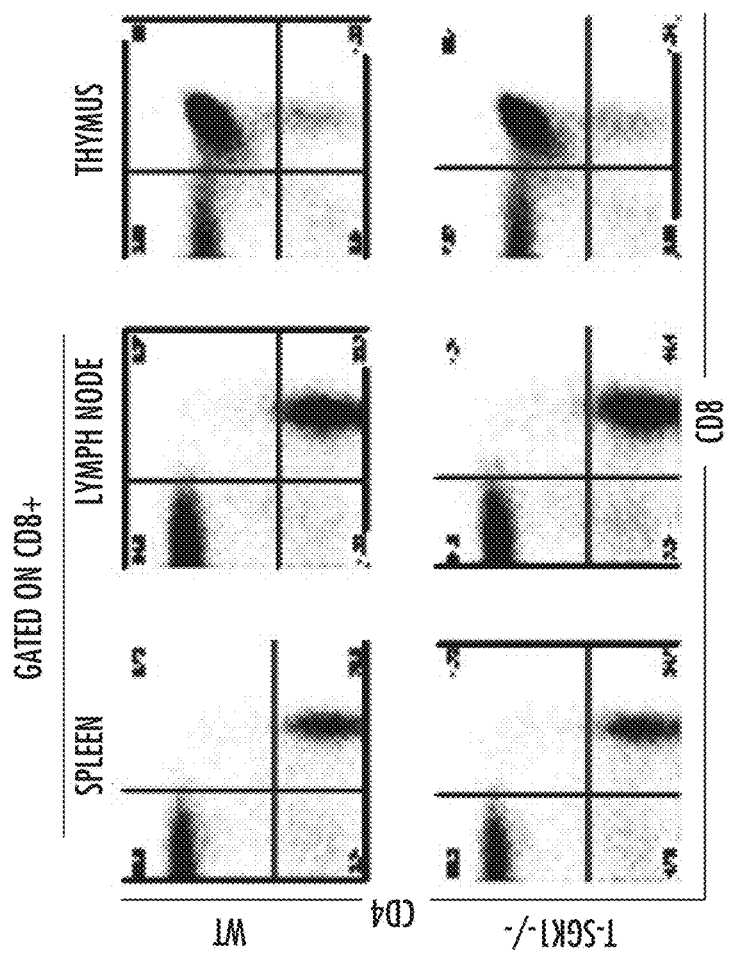
FIG. 4A-4B show T-SGK1-/- mice have reduced number of T cells in the spleen and lymph nodes, but have an expanded B cell compartment. (4A) Flow cytometric phenotyping of Wt and T-SGK1$^{-/-}$ splenocytes, lymph nodes, and (4B) splenocytes, lymph nodes, and thymus with CD8+ gating.
Figure 4A:
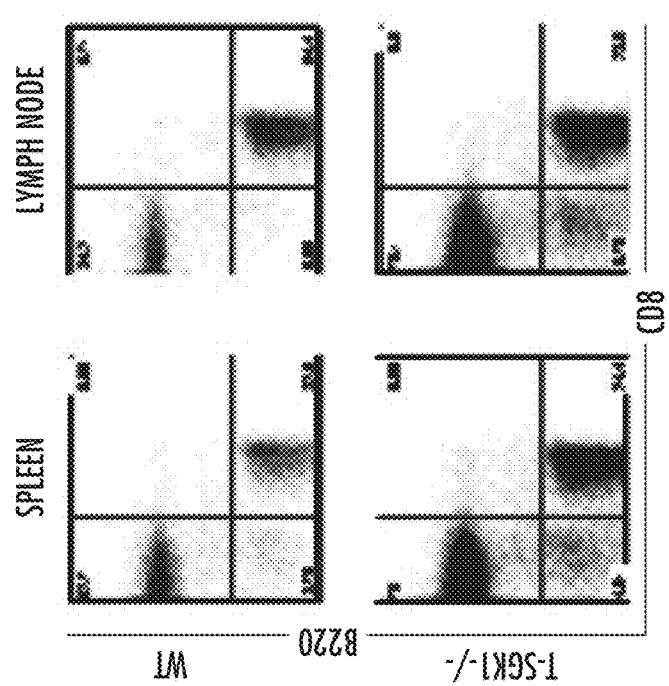
Figure 5:
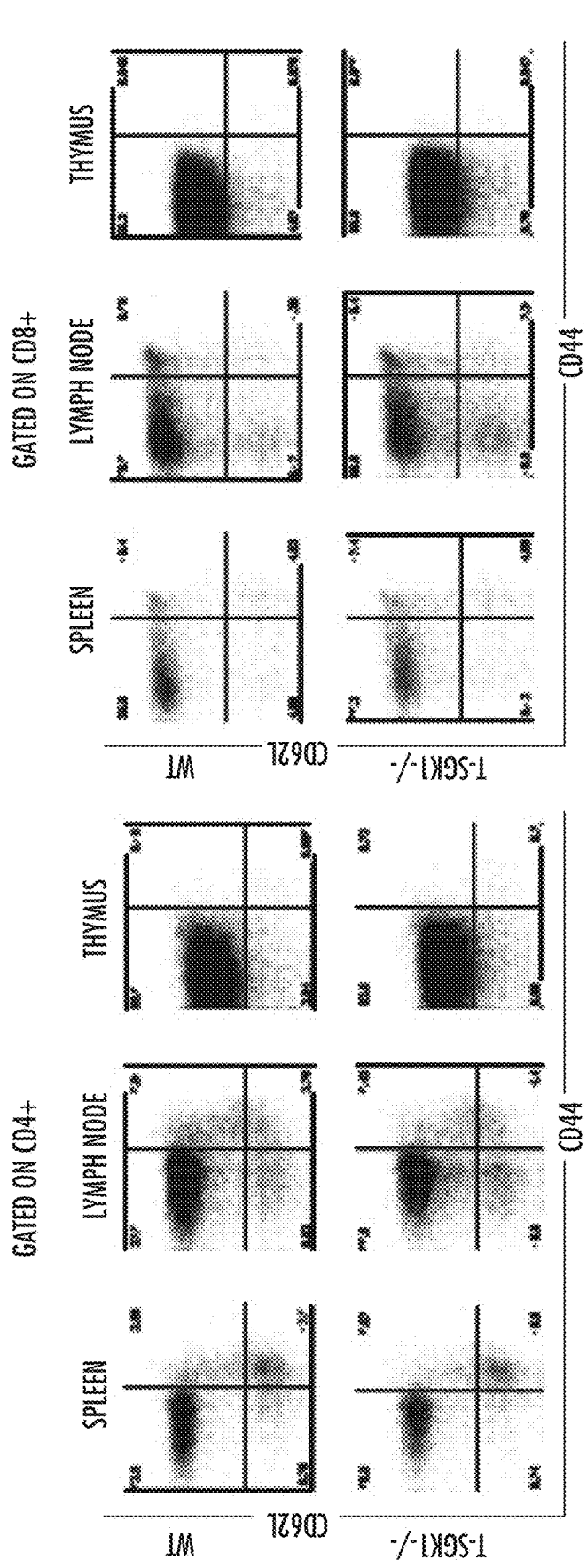
FIG. 5 illustrates T-SGK1-/- mice have a similar number of naïve T cells compared to Wt mice. Flow cytometric phenotyping of Wt and T-SGK1-/- splenocytes, lymph nodes, and thymus.
Figure 6:
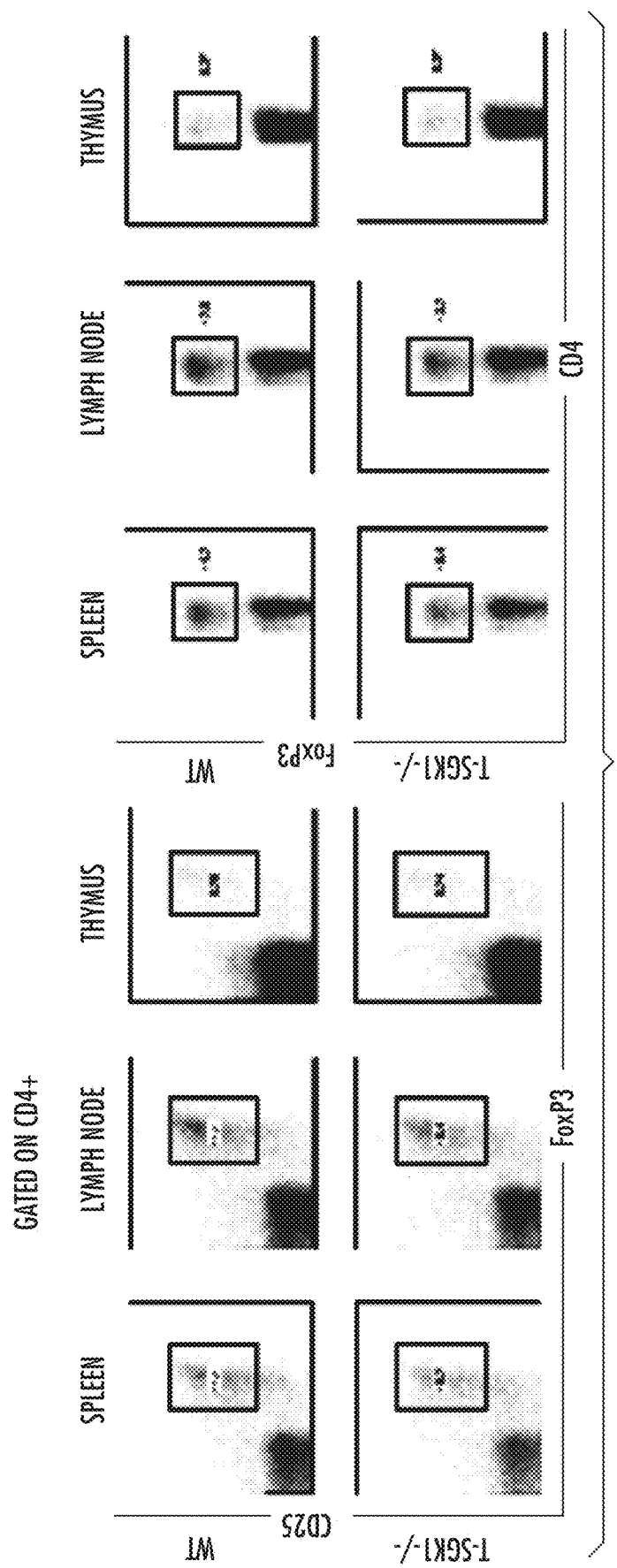
FIG. 6 shows T-SGK1-/- mice have a similar number of natural regulatory T cells in the spleen and lymph nodes compared to Wt mice. Flow cytometric phenotyping of Wt and T-SGK1-/- splenocytes, lymph nodes, and thymus.
Figure 7:
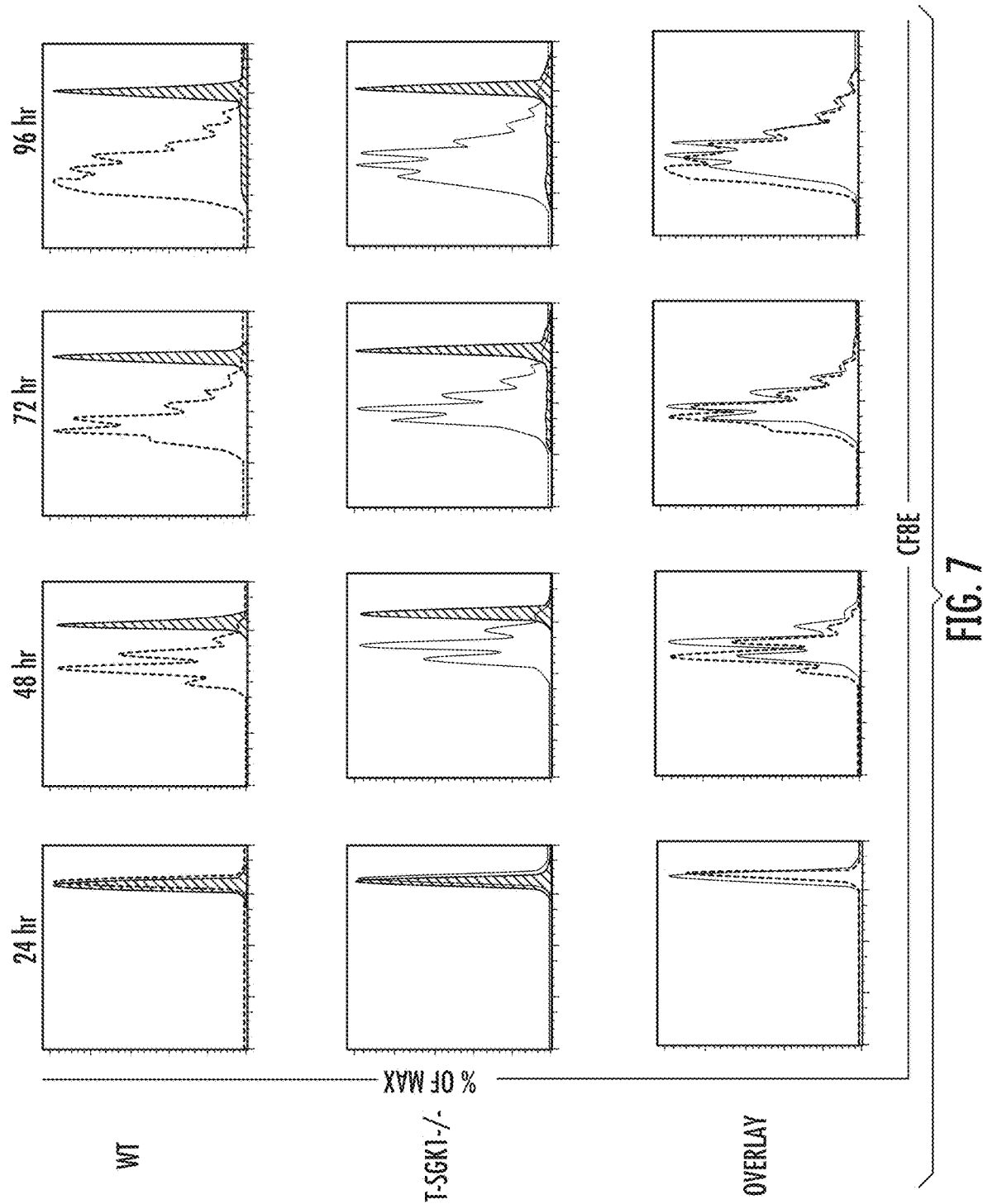
FIG. 7 depicts T-SGK1-/- have a similar number of IL17-producing cells in peyer's patches compared to Wt mice. Flow cytometric phenotyping of Wt and T-SGK1-/- peyer's patches.
Figure 8A:
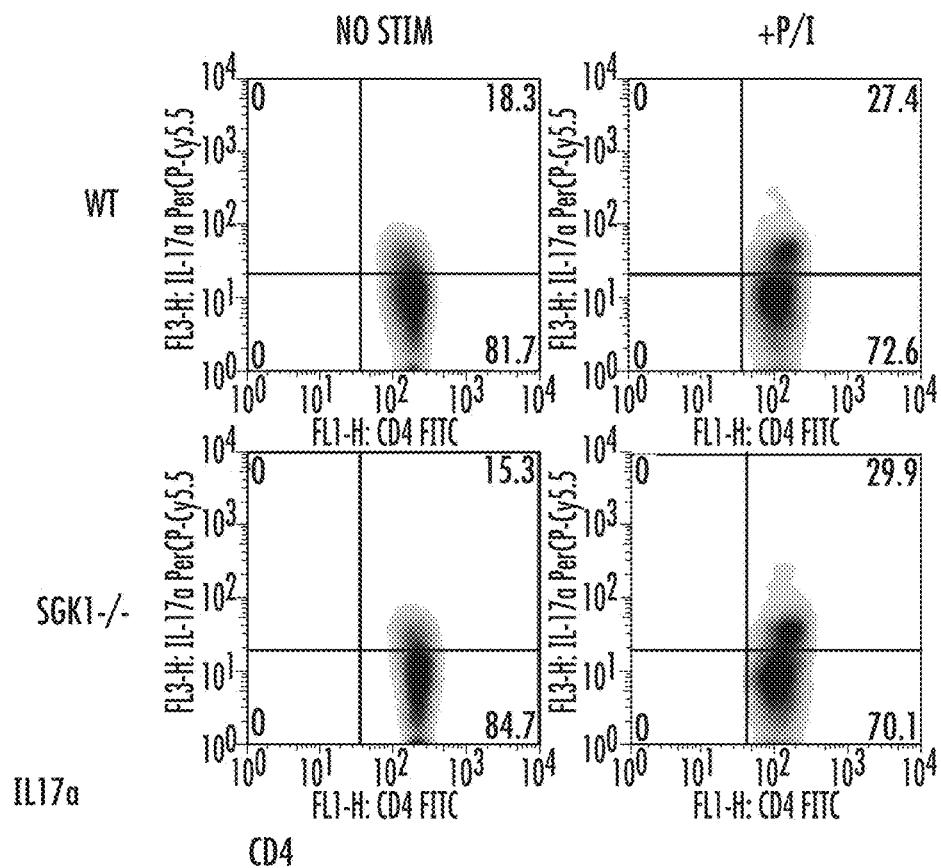
FIG. 8A-8B show CD4+ T cells from T-SGK1-/- mice have reduced proliferative capacity in vitro. CD4+ T cells were isolated from Wt or T-SGK1-/- mice, stained with carboxyfluorescein succinimidyl ester (CFSE), and stimulated with irradiated syngeneic APCs and 1 mg/mL anti-CD3 for 24, 48, 72 or 96 h (8A). Flow cytometric phenotyping of Wt and T-SGK1-/- CD4+ T cells (8B).
Figure 8B:
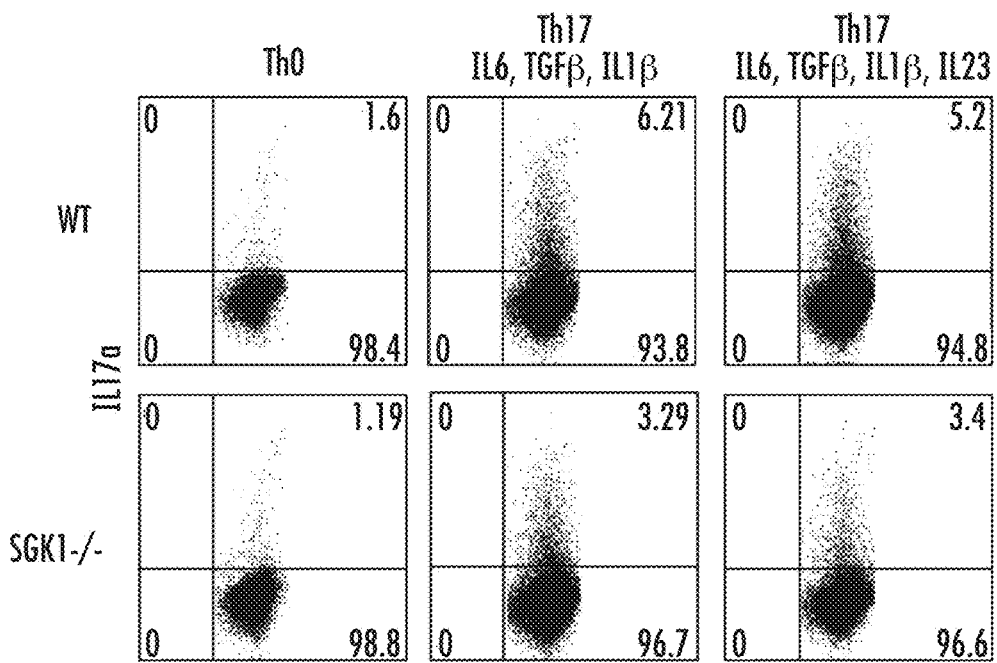

Determination of the functional consequences of deleting SGK1 in CD4+ T cells. Unlike T-Rictor−/− mice, which have a normal lymphocyte compartment, fewer CD3+ T cells were observed in the spleen and lymph nodes of T-SGK1−/− mice (FIGS. 4, 5). Furthermore, T-SGK1−/− mice had a reduced ratio of CD4+ relative to CD8+ T cells in peripheral lymphoid organs. Despite this reduction in the percentages of T cells, T-SGK1−/− mice have similar percentages of natural regulatory T cells and IL-17 producing CD4+ cells in Peyer's patches of the small intestine (FIGS. 6, 7). In addition to their reduced number of T cells, it was also found that CD4+ T cells from T-SGK1−/− mice displayed a slightly reduced rate of proliferation when stimulated with anti-CD3 and irradiated autologous antigen presenting cells (APCs) (FIG. 8). Despite their reduced proliferation, it was found that CD4+ T cells from T-SGK1−/− mice displayed robust cytokine production.

Figure 9:
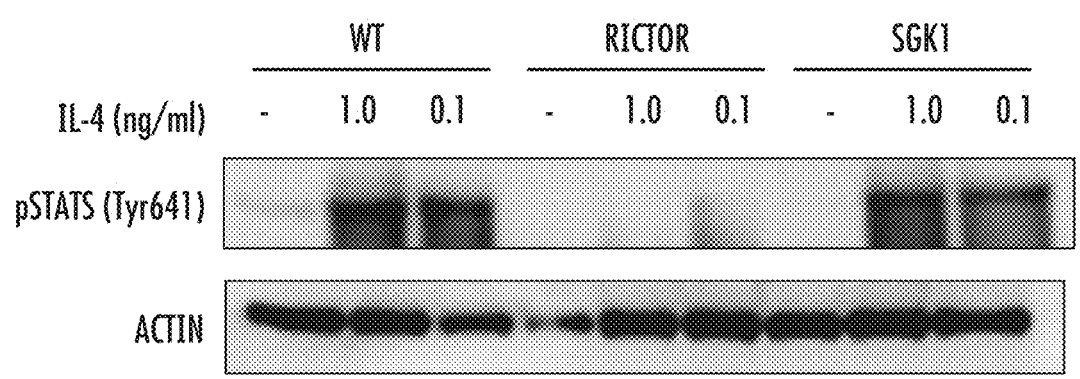
FIG. 9 shows CD4+ T cells from T-SGK1-/- mice inappropriately secrete IFN-γ under Th2 skewing conditions. Production of IFN-γ by ELISA. Naïve CD4+ CD4P T cells from Wt, T-Rictor-/-, and T-SGK1-/- mice were isolated based on expression of CD44 and CD62L (data not shown). Cells were stimulated with irradiated autologous APCs, 1 μg 1 μg 1 mg/mL anti-CD3, and either (Th0) IL-2 or (Th1) IL-12, IFN-γ, and anti-IL-4, or (Th2) IL-4, anti-IFN-γ, and anti-IL-12p40 skewing conditions for 2 days. After stimulation, cells were rested in IL-2 prior to restimulation overnight with anti-CD3 and anti-CD28. Supernatants were collected as assayed for the secretion of IFN-γ by ELISA.

Like T-Rictor−/− mice, T-SGK1−/− mice constitutively adopt a Th1 phenotype and inappropriately produce IFN-γ when stimulated in the presence of IL-4 under Th2 skewing conditions (FIGS. 3B, 9). In addition, CD4+ T cells from T-SGK1−/− mice fail to adopt a Th2 phenotype and do not produce IL-4, similar to T-Rictor−/− mice. In addition to adopting a Th1 cytokine profile, it was observed that both T-SGK1−/− and T-Rictor−/− mice express higher levels of the master Th1 transcription factor Tbet (FIGS. 3D, 3E). Consistent with their inability to make IL-4, both T-SGK1−/− and T-Rictor−/− failed to upregulate the Th2 lineage-specific transcription factor GATA3 (FIG. 3E). Collectively, these results demonstrate that loss of SGK1 in CD4+ T cells phenocopies loss Rictor, which is consistent with reports in other systems that SGK1 is a downstream mediator of mTORC2 signaling.

Example 3

Figure 10:
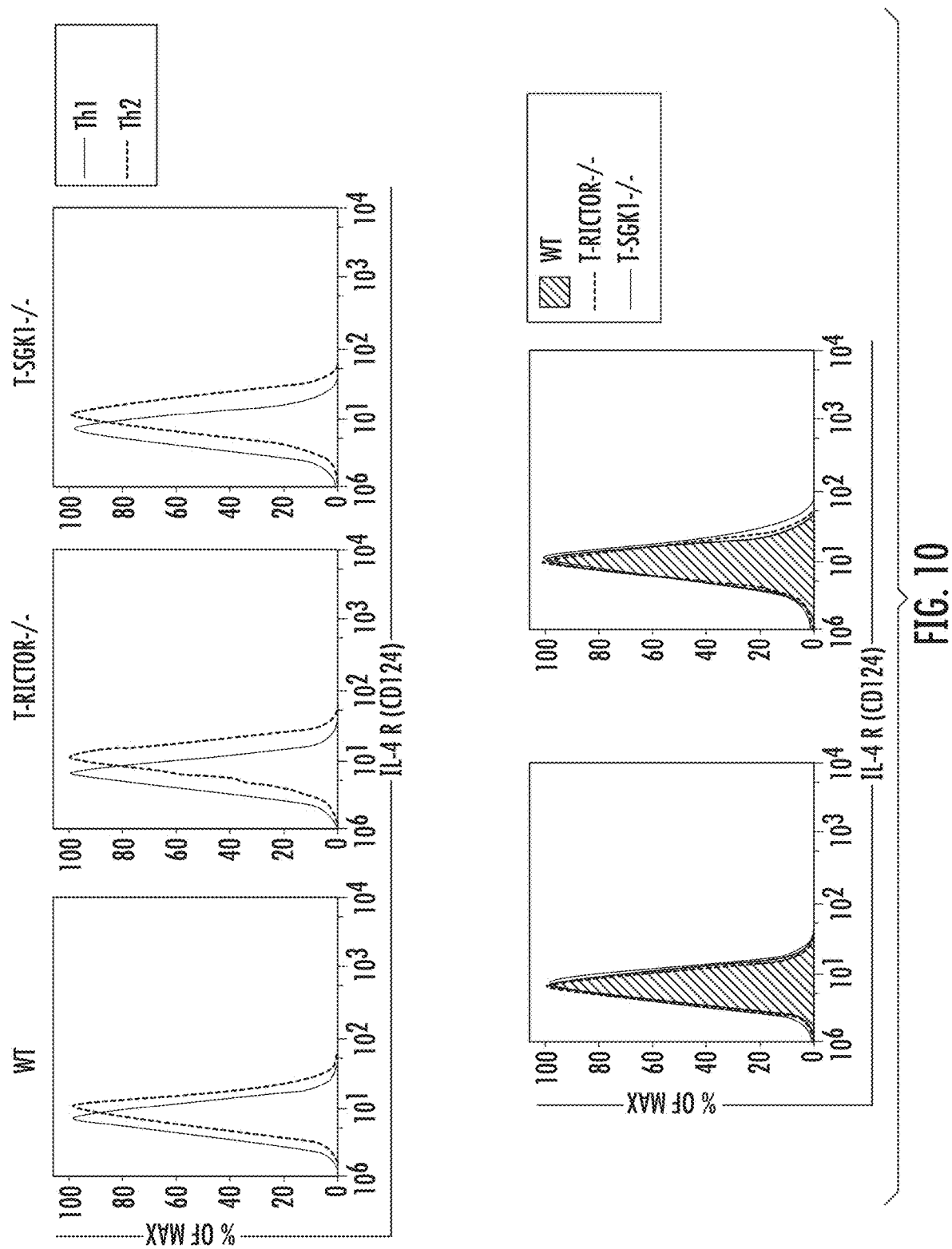
FIG. 10 depicts the loss of SGK1 does not affect signaling through STAT6, but loss of TORC2 activity results in loss of STAT6 activity. CD4+ T cells were isolated from Wt, T-Rictor-/- and T-SGK1-/- mice and serum starved for 1 hour, and then IL-4 was added to the cells for 20 minutes. Cells were lysed and immunblotted for STAT6 (Tyr641), and actin is included as a loading control.

The determination of the biochemical mechanism by which SGK1 reciprocally regulates Th1 and Th2 differentiation. The inventors have previously shown that CD4+ T cells from T-Rictor−/− mice show diminished phosphorylation of STAT6 in response to IL-4. However, when CD4+ T cells from T-SGK1−/− mice were treated with IL-4, phosphorylation of STAT6 at tyrosine 641 was observed (FIG. 10), suggesting that SGK1 was regulating Th2 differentiation via some other mechanism. Previous studies on the role of SGK1 in renal epithelial cells have demonstrated that SGK1 negatively regulates the HECT-type E3 ligase neural precursor cell expressed, developmentally down-regulated gene 4-like (NEDD4L) by phosphorylation at serine 342 and serine 448. A closely related homolog of NEDD4L is the ubiquitin ligase Itch, which has been shown to interact with the Nedd4 family-interacting protein 1 (Ndfip1) adapter protein to mediate polyubiquitination of JunB, a transcription factor that is essential for Th2 development. Therefore, it was investigated whether the defect in Th2 differentiation that was observed in T-SGK1−/− mice could be due to increased ubiquitination and destruction of JunB by NEDD4L. It has previously been shown that JunB is upregulated under Th2 skewing conditions by 72 hours during T cell activation.

Figure 11C:
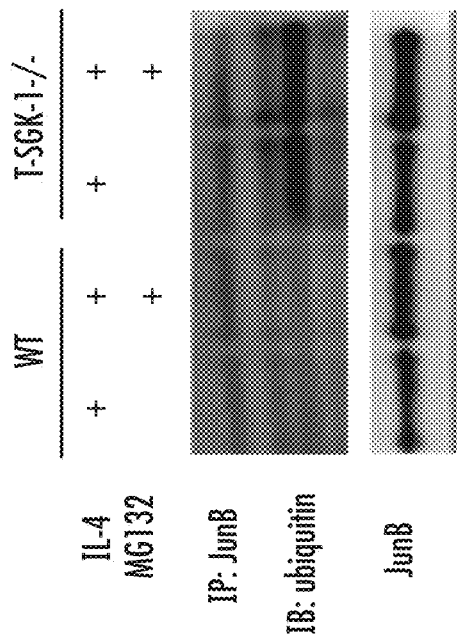
Figure 11A:
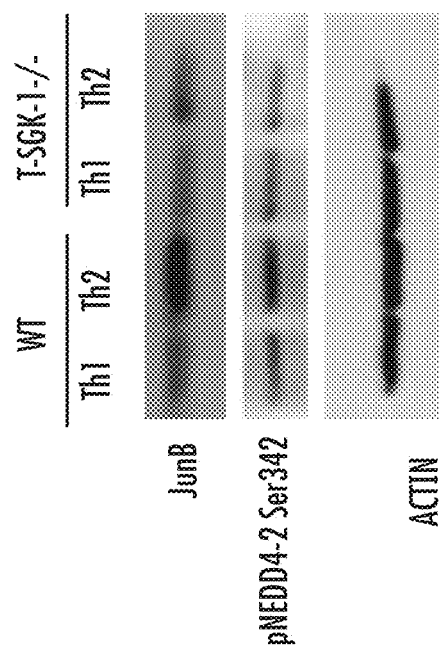
Figure 11B:
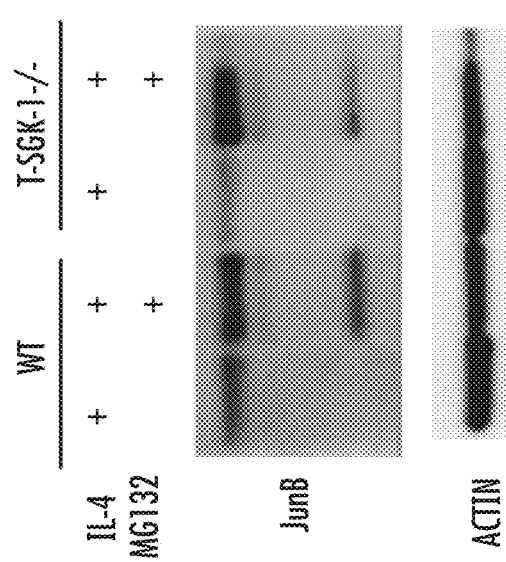
Figure 11D:
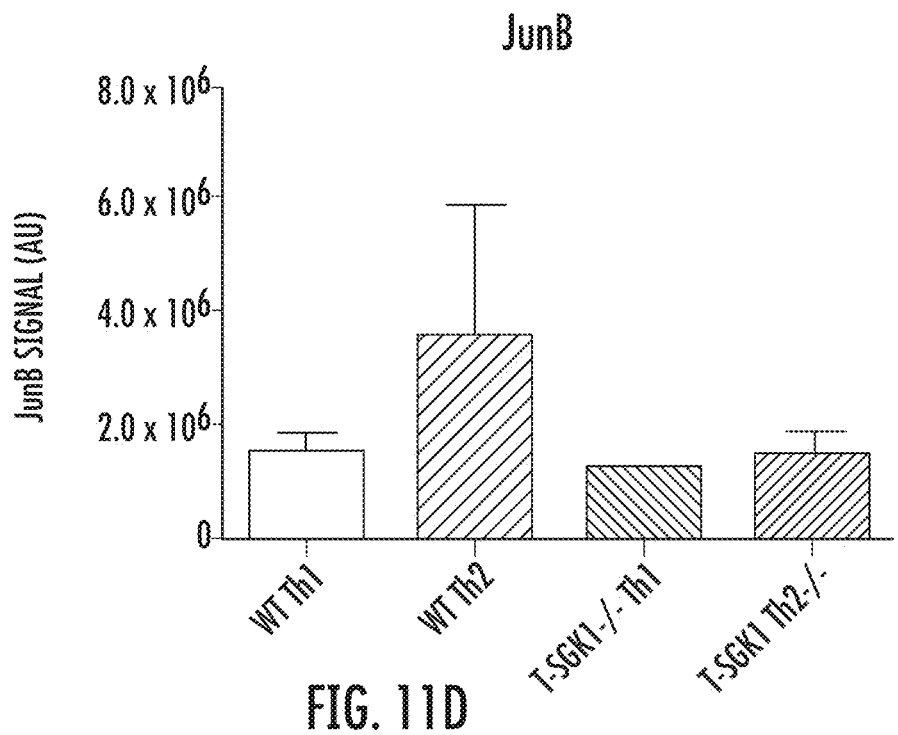
Figure 11E:
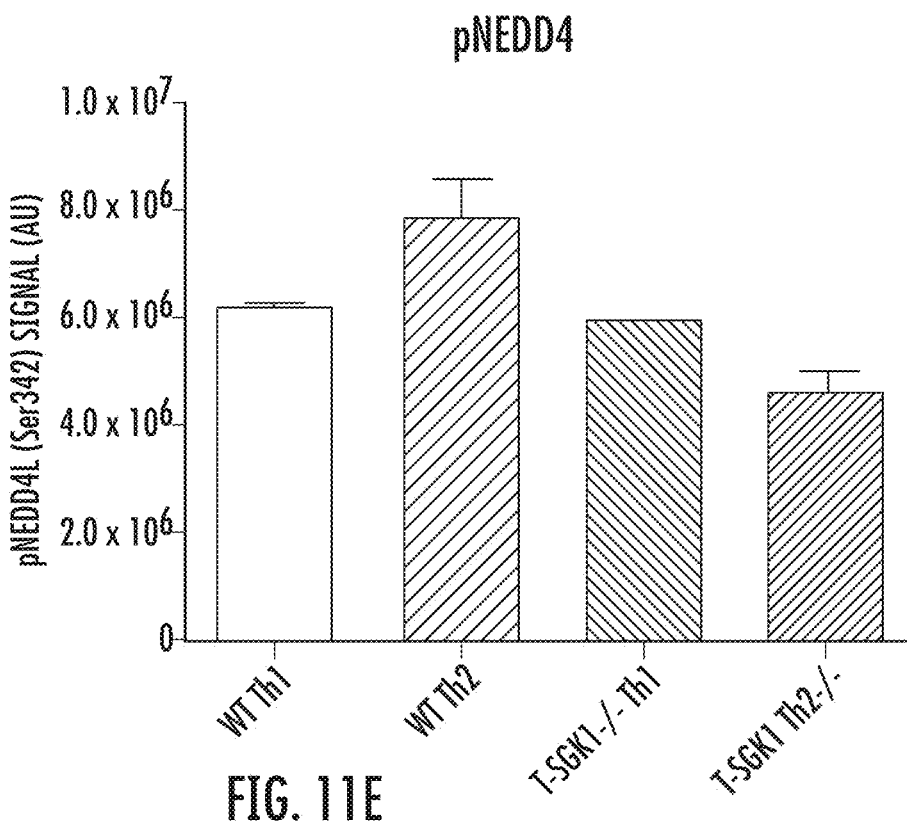
Figure 11F:
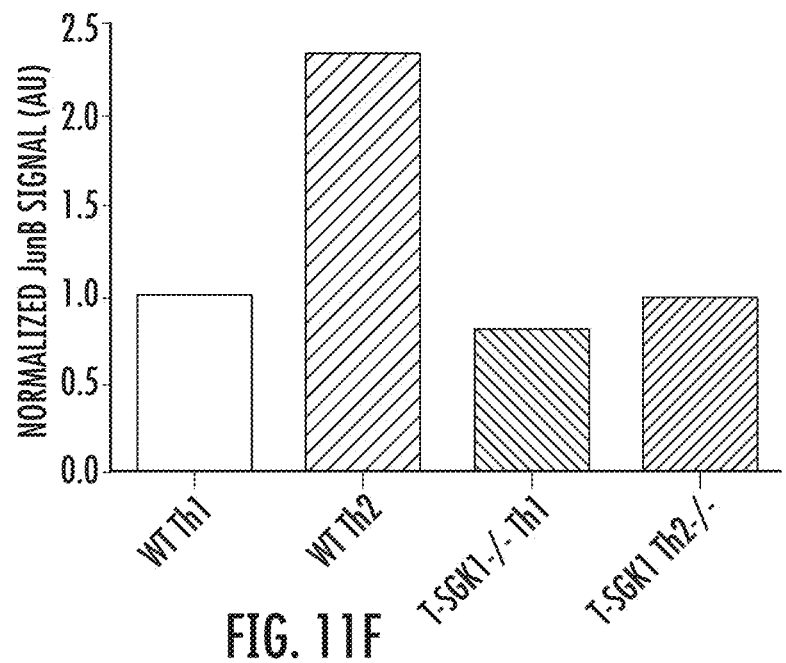
Figure 11G:
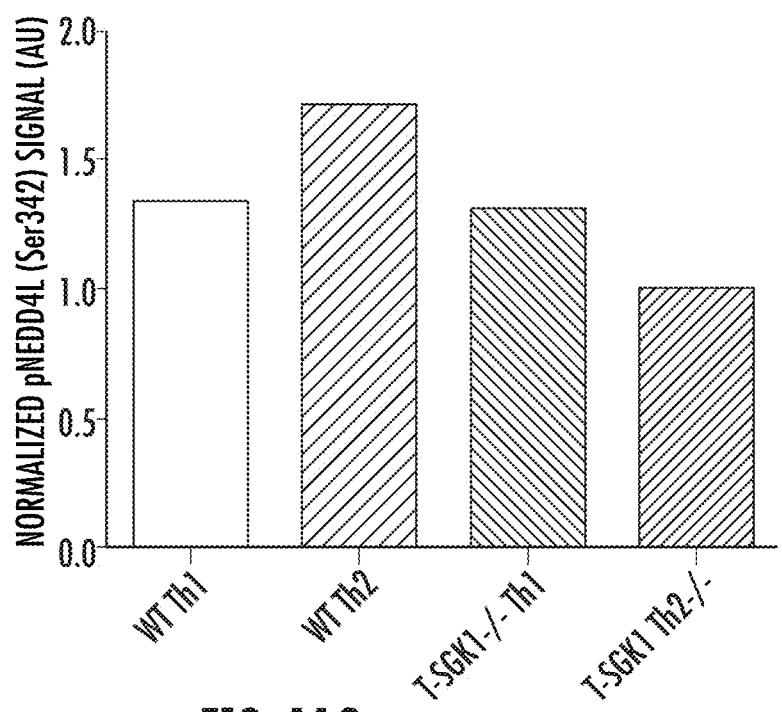

CD4+ T cells from Wt and T-SGK1−/− mice were activated under Th1 or Th2 skewing conditions for 72 hours, cells were lysed and separated into nuclear and cytoplasmic fractions, and the levels of JunB protein expression were assayed by immunoblot. It was observed that JunB protein levels were decreased under both Th1 and Th2 skewing conditions in T-SGK1−/− mice (FIG. 11A). Next, it was investigated whether decreased expression of JunB in T-SGK1−/− T cells was due to increased degradation of the protein. It was found that JunB levels increased in T-SGK1−/− T cells upon addition of the proteasome inhibitor MG132 to cultures of CD4+ T cells that had been activated under Th2 skewing conditions (FIG. 11B). To confirm that JunB degradation was due to increased ubiquitination, JunB was immunoprecipitated in Wt and T-SGK1−/− CD4+ T cells and immunoblotted for ubiquitin. It was found that JunB was not ubiquitinated under Th2 conditions in Wt mice, but JunB ubiquitination was markedly enhanced in the absence of SGK1 (FIG. 11C). Furthermore, we found that NEDD4L co-immunoprecipitated with JunB under these conditions. Altogether, these results show that T-SGK1−/− CD4+ T cells fail to adopt a Th2 phenotype because SGK1 negatively regulates an E3 ligase that targets JunB for destruction.

Example 4

While this mechanism provides an explanation for why T-SGK1−/− CD4+ T cells cannot differentiate towards a Th2 phenotype, it does not explain why CD4+ T cells constitutively adopt a Th1 fate in the absence of SGK1. It has previously been reported that mice deficient in T cell factor 1 (TCF1) produce more IFN-γ, much like T-SGK1−/− mice, so it was investigated whether TCF1 was regulated by SGK1 during helper T cell differentiation.

Wt and T-SGK1−/− CD4+ T cells were skewed under Th1 and Th2 conditions, and assayed for protein levels of TCF1 by immunoblot. Interestingly, it was found that the long isoforms of TCF1 were decreased in T-SGK1−/− under both Th1 and Th2 skewing conditions, but there was no difference in expression of the short isoforms of this protein (FIG. 11H). The long isoforms of TCF1 contain an additional β-catenin binding domain (FIG. 11I), and these isoforms specifically promote the acquisition of a Th2 phenotype by promoting expression of GATA3 and repressing IFN-γ.

To determine whether SGK1 was regulating TCF1 at the transcriptional level, primers were designed to specifically detect mRNA encoding the long and short isoforms of this protein. We found that there was no difference in the short isoforms of TCF1 mRNA present in Wt and T-SGK1−/− T cells, however, transcripts of the long isoforms of TCF1 could not be detected in T-SGK1−/− T cells (FIG. 11J). These results indicated that SGK1 regulates transcription of the long isoforms of TCF1, and therefore in the absence of SGK1, TCF1 is no longer able to repress IFN-γ under Th2 conditions.

Next, rescue of the phenotype of T-SGK1−/− CD4+ T cells was attempted by overexpressing the long isoformsisoformsisforms of TCF1 via retroviral transduction with an MSCV-based vector containing full length TCF1 (FL-TCF1) and a human CD8 reporter. CD4+ T cells from Wt and T-SGK1−/− mice were stimulated under Th2 conditions, transduced, then expanded and rested in IL2. Transduced cells were sorted by selecting for surface expression of human CD8, then restimulated the cells and assayed for the production of IFN-γ by intracellular staining. It was found that T-SGK1−/− T cells that were rescued with FL-TCF1 no longer inappropriately produced IFN-γ under Th2 conditions (FIG. 11K) indicating that the role of SGK1 in repressing Th1 differentiation is to promote transcription of the long-isoforms of TCF1.

Example 5

As the role of mTORC2 and SGK1 in regulating the differentiation of helper T cells was now defined in vitro, a confirmation that this paradigm in an in vivo model of Th2-mediated disease was undertaken. A study of allergic asthma was chosen because Th2 cells are involved in the early pathogenesis of this disease, and Th1 responses are thought to be protective in this setting. Therefore, it was hypothesized that both T-Rictor−/− and T-SGK1−/− mice would be resistant to allergic asthma. Mice were immunized OVA in aluminum hydroxide (alum) on days 0 and 7, and then were challenged mice intranasally with OVA protein on days 15, 16, and 17, prior to sacrifice on day 18. Wt mice mounted a stereotypic Th2 response to this allergic stimulus, characterized by IL-4 in bronchoalveolar lavage (BAL) and OVA-specific IgG1 in serum (FIGS. 12A, 12B). By contrast, T-Rictor−/− and T-SGK1−/− mice did not demonstrate the presence of IL-4 in BAL and instead had detectable titers of OVA-specific IgG2a (FIGS. 12A, 12C). Furthermore, lung lymphocytes from T-Rictor−/− and T-SGK1−/− mice inappropriately produced IFN-γγIFNγ when stimulated ex vivo (FIG. 12D).). This inappropriate immune response appeared to protect T-Rictor−/− and T-SGK1−/− mice from disease, because lung histology from these mice did not show the pathologic changes which are associated with allergic asthma such as lymphocytic infiltration and epithelia hyperplasia that were observed in Wt animals (FIG. 12 E).

Inasmuch as loss of mTORC2 activity abrogates Th2 differentiation in vitro, these results demonstrate that mTORC2 signaling via SGK1 plays a critical role in IL4 production and Th2 differentiation in the pathologic setting of allergic asthma in vivo.

Example 6

Figure 13B:
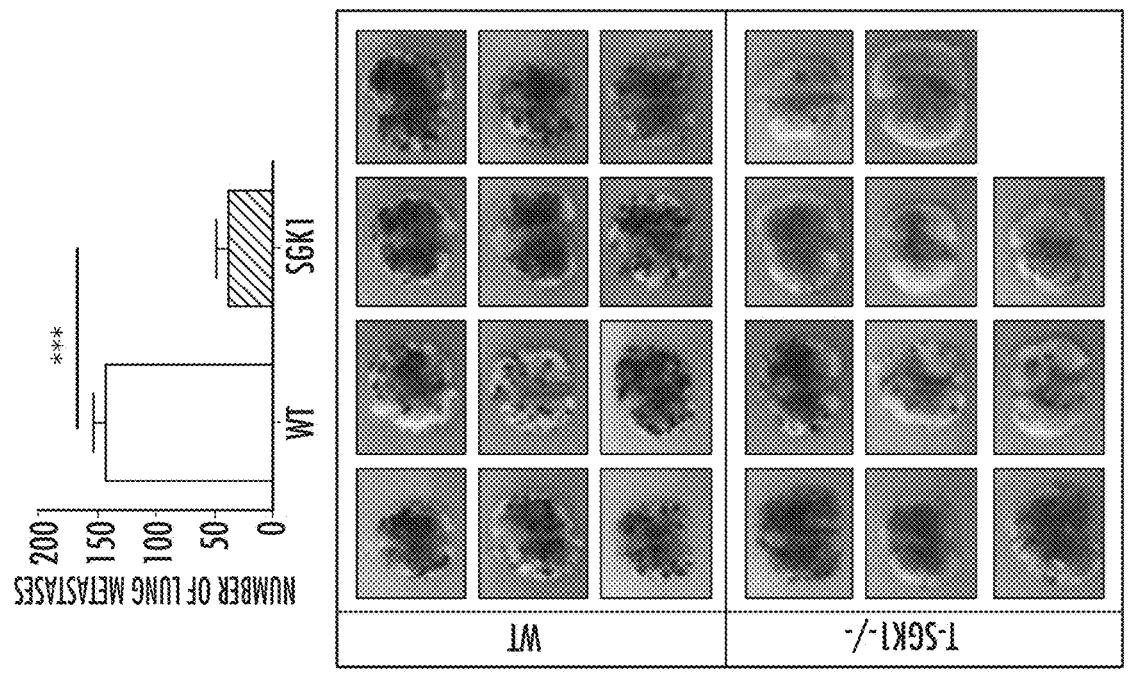
Figure 13A:
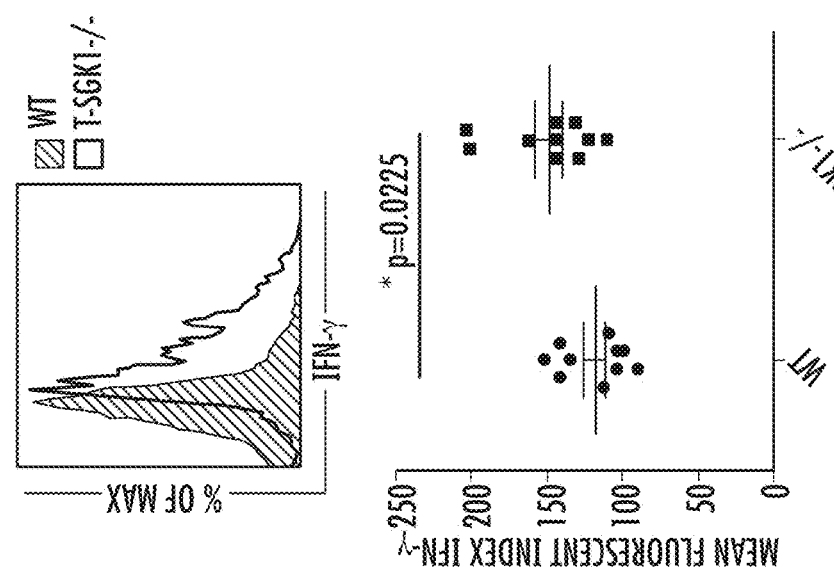
Figure 14A:
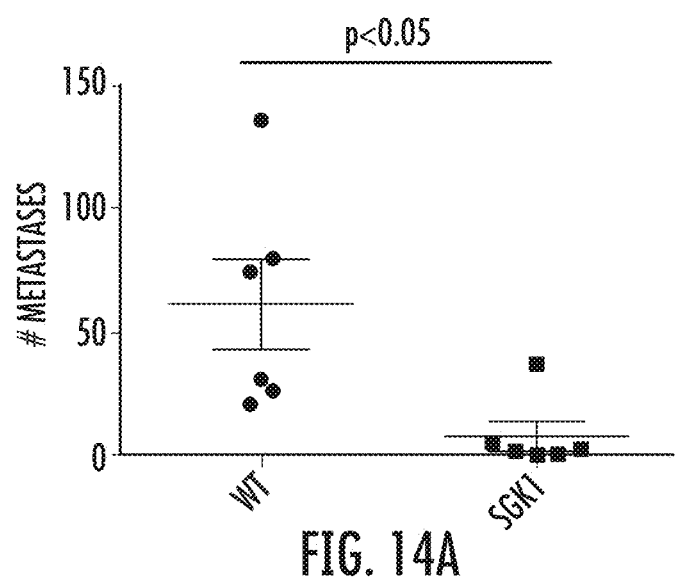
FIG. 14A-14B depict that vaccination enhances anti-tumor immunity in T-SGK1−/− mice. Wt (Wt) or T-SGK1−/− were vaccinated with $1 \times 10^6$ plaque forming units (pfu) of vaccinia (VAC) virus that had been genetically engineering to express the model antigen chicken ovalbumin (OVA), hereafter referred to as VAC-OVA. On Day 7 post-vaccination, mice were challenged by injecting 300,000 B16 melanoma cells that had also been genetically engineered to express OVA, hereafter referred to as B16-OVA. Lungs were harvested on Day 28 to count metastases, which are quantified in (14A) and shown as gross images in (14B).
Figure 14B:
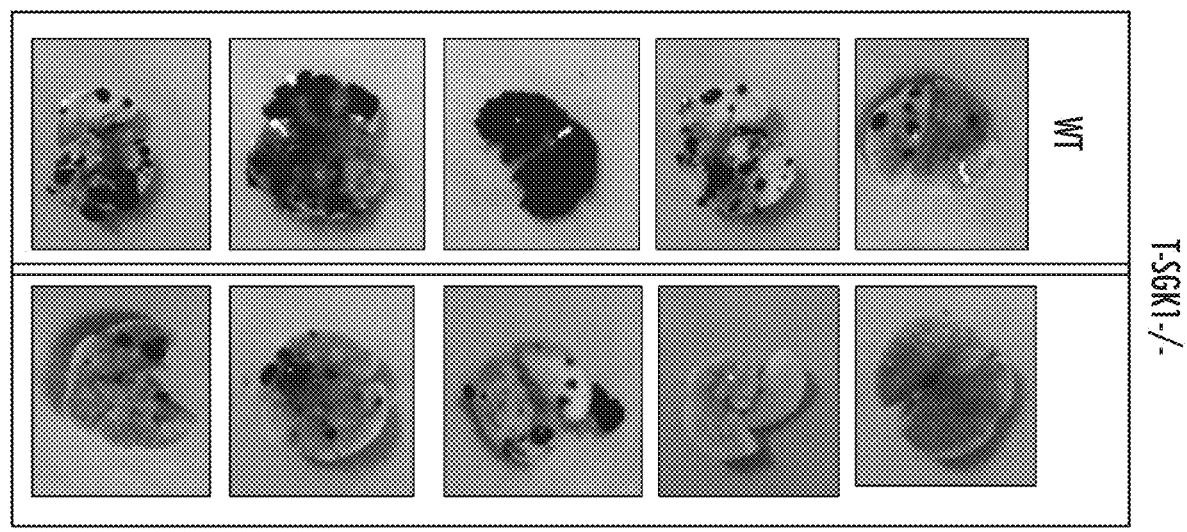
Figure 15A:
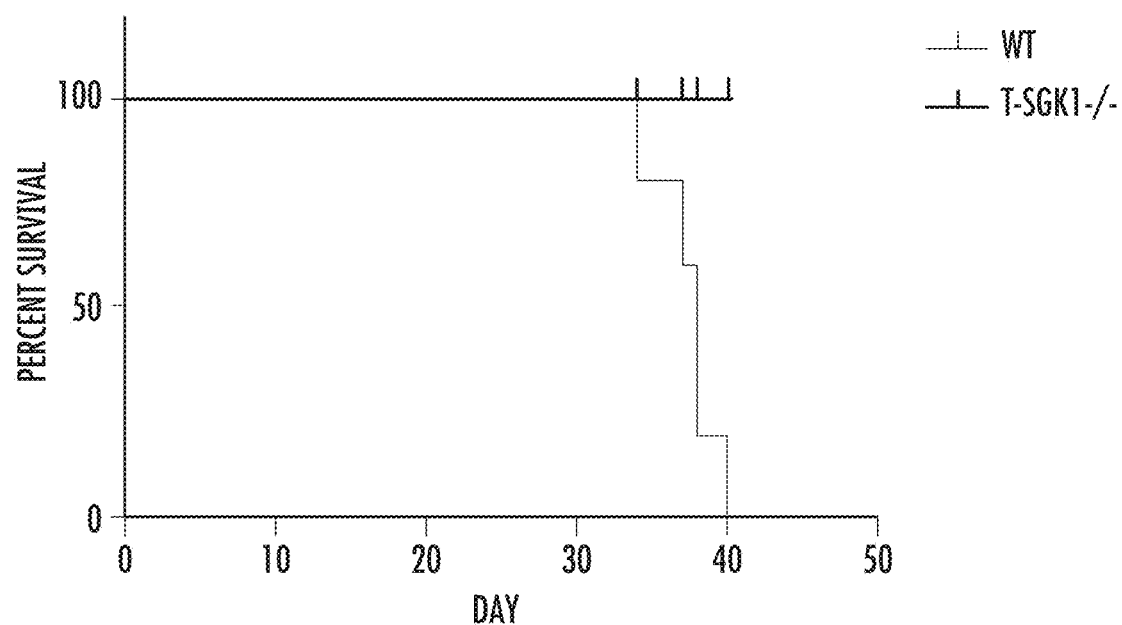
FIG. 15A-15B show that vaccination enhances survival of T-SGK1−/− mice in a B16-OVA model of lung metastasis. Wt or T-SGK1−/− were vaccinated with $1 \times 10^6$ pfu of VAC-OVA. On Day 7 post-vaccination, mice were challenged by injecting 30,000 B16-OVA melanoma cells intravenously. Survival was the measured endpoint of the experiment (which is ongoing), but current results are shown in (15A). Lungs were harvested from deceased mice and gross images are shown in (15B).
Figure 15B:
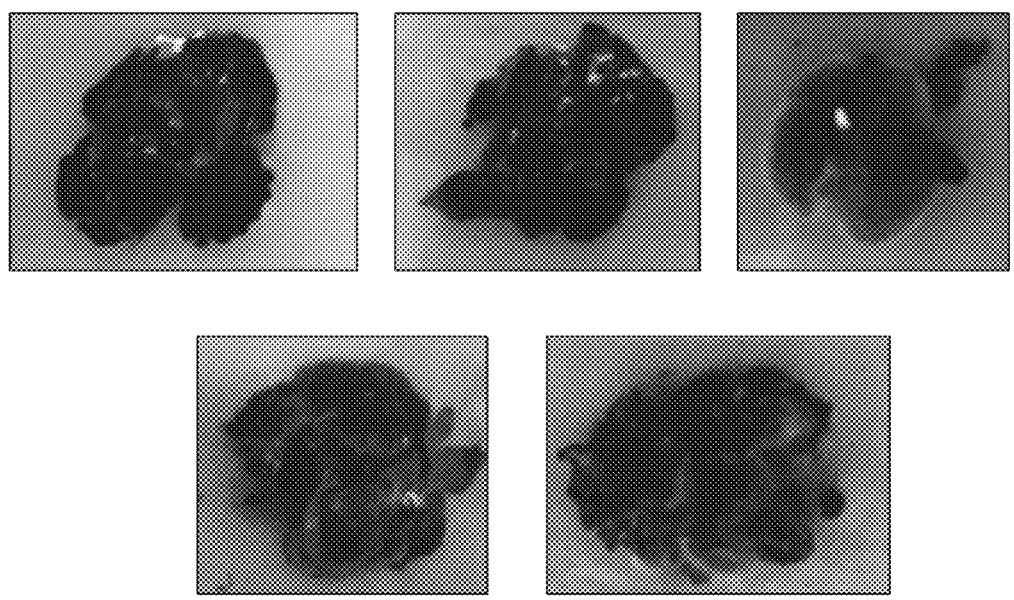

Loss of SGK1 drives CD4+ T cells to adopt a Th1 phenotype in vivo, so it was hypothesized that T-SGK1−/− mice would mount a more robust Th1-mediated immune response to B16 melanoma. Wt and T-SGK1−/− mice were injected with 5×10$^5$ B16 melanoma cells intravenously, and harvested lungs 21 days later. Loss of SGK1 resulted in half as many lung metastases and decreased lung mass, which is another measure of tumor burden (FIGS. 13A, 13B, 13E). It was found that T-SGK1−/− mice had fewer lung metastases because their T cells (both CD4+ and CD8+) produced more IFN-γ. These results indicate that inhibitors of SGK1 can be used as an adjuvant for tumor vaccines or in addition to chemotherapy.

Example 7

In accordance with one or more embodiments, the present invention provides mechanistic evidence for how mTORC2 controls helper T cell fate through activation of SGK1. It is now shown that SGK1 negatively regulates the NEDD4L E3 ligase to prevent destruction of the Th2 transcription factor JunB. While not being limited to any particular mechanism, this paradigm can represent a general mechanism by which mTOR regulates AGC kinases like SGK1, Akt, and S6 Kinase, which in turn regulate E3 ligases to control the degradation of lineage-specific transcription factors during T cell differentiation. It is shown that mTOR's role in T cell differentiation is to serve as a regulator of E3 ligases which mediate the destruction of these transcription factors, in order to drive a T cell towards a particular fate.

The present invention also provides that SGK1 negatively regulates Th1 differentiation by repressing transcription of TCF1. Whether SGK1 acts directly at the TCF1 locus or indirectly via another transcriptional repressor will require further study.

In summary, these the present invention demonstrates that SGK1 selectively and reciprocally regulates helper T cell differentiation downstream of mTORC2. The methods disclosed herein show that targeting SGK1 is beneficial in the setting of autoimmune diseases that are mediated by Th2 immune responses, such as in the setting of allergic asthma. Conversely, inhibiting SGK1 is also useful in diseases in which a Th1 response is therapeutic, such as in tumors. By defining SGK1 as a downstream node in the mTOR signaling network, the present invention provides further insight into how this pathway regulates T cell differentiation in physiologic settings, in addition to how this pathway can be manipulated in pathologic settings to achieve a productive immune response.

Example 8

Vaccination in combination with inhibition of SGK1 can further enhance tumor immunity. It was previously shown that inhibition of SGK1 alone enhances anti-tumor immunity (see Example 6 and FIG. 13). It was then determined whether inhibition of SGK1 can enhance vaccine induced immunity. Wt or T-SGK1−/− were vaccinated with 1×10$^6$ pfu of VAC virus that had been genetically engineering to express OVA, hereafter referred to as VAC-OVA. On Day 7 post-vaccination, mice were challenged by injecting 300,000 B16 melanoma cells that had also been genetically engineered to express OVA, hereafter referred to as B16-OVA. Lungs were harvested on Day 28 to count metastases, which are quantified in (14A) and shown as gross images in (14B). T-SGK1-/- mice have significantly fewer lung metastases as compared to Wt mice. Thus, this data shows that vaccination in combination with inhibition of SGK1 can further enhance tumor immunity.

Example 9

Vaccination enhances survival of T-SGK1-/- mice in a B16-OVA model of lung metastasis. As in Example 8, Wt or T-SGK1-/- were vaccinated with 1×10$^6$ pfu of VAC-OVA. On Day 7 post-vaccination, mice were challenged by injecting 30,000 B16-OVA melanoma cells intravenously. Survival was the measured endpoint of the experiment (which is ongoing), but current results are shown in (15A). Lungs were harvested from deceased mice and gross images are shown in (15B). T-SGK1-/- mice have significantly prolonged survival in a model of B16 melanoma. All Wt mice are dead by Day 40, but T-SGK1-/- mice survive.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for enhancing a Th1-mediated immune response in a subject suffering from melanoma comprising administering to the subject, a pharmaceutical composition comprising a serum-glucocorticoid regulated kinase 1 (SGK1) inhibitor selected from the group consisting of the following derivatives of pyrrolo[2,3b]pyridine: 2-ethyl-4-(5-phenyl-1H-pyrrolo[2,3-b]pyridin-3-yl)benzoic acid, 2-(methylamino)-4-(5-phenyl-1H-pyrrolo[2,3-b]pyridin-3-yl)benzoic acid, 2-(dimethylamino)-4-(5-phenyl-1H-pyrrolo[2,3-b]pyridin-3-yl)benzoic acid, 2-cyclopentyl-4-(5-phenyl-1H-pyrrolo[2,3-b]pyridin-3-yl)benzoic acid, 4-(5-phenyl-1H-pyrrolo[2,3-b]pyridin-3-yl)-2-propylbenzoic acid, 2,6-difluoro-4-(5-phenyl-1H-pyrrolo[2,3-b]pyridin-3-yl)benzoic acid, 2,6-dimethyl-4-(5-phenyl-1H-pyrrolo[2,3- b]pyridin-3-yl)benzoic acid, 2-(2-propyl)-4-(5-phenyl-1H-pyrrolo[2,3-b]pyridin-3-yl)benzoic acid, 6-(5-phenyl-1H-pyrrolo[2,3-b]pyridin-3-yl)-1H-indazole, 2-(2-methylpropyl)-4-(5-phenyl-1H-pyrrolo[2,3-b]pyridin-3-yl) benzoic acid, and 2-methyl-4-(5-phenyl-1H-pyrrolo[2,3-b]pyridin-3-yl)benzoic acid, and a pharmaceutically acceptable carrier, in an effective amount such that the Th1-mediated immune response in the subject is increased when compared to a non-treated subject.

2. The method of claim 1, wherein the derivative of pyrrolo[2,3b]pyridine is 2-cyclopental-4-(5-phenyl-1H-pyrrolo[2,3b]pyridine-3yl-)-benzoic acid.

3. The method of claim 1, wherein the method further comprises administering to the subject a pharmaceutical composition comprising at least one other therapeutic agent, either before, concomitant with, or subsequent to administration of the pharmaceutical compositions comprising the SGK1 inhibitor to the subject.

4. A method for treating melanoma in a subject comprising administering to the subject, a pharmaceutical composition comprising a serum-glucocorticoid regulated kinase 1 (SGK1) inhibitor selected from the group consisting of the following derivatives of pyrrolo[2,3b]pyridine: 2-ethyl-4-(5-phenyl-1H-pyrrolo[2,3-b]pyridin-3-yl)benzoic acid, 2-methylamino)-4-(5-phenyl-1H-pyrrolo[2,3-b]pyridin-3-yl)benzoic acid, 2-(dimethylamino)-4-(5-phenyl-1H-pyrrolo[2,3-b]pyridin-3-yl)benzoic acid, 2-cyclopentyl-4-(5-phenyl-1H-pyrrolo[2,3-b]pyridin-3-yl)benzoic acid, 4-(5-phenyl-1H-pyrrolo[2,3-b]pyridin-3-yl)-2-propylbenzoic acid, 2,6-difluoro-4-(5-phenyl-1H-pyrrolo[2,3-b]pyridin-3-yl)benzoic acid, 2,6-dimethyl-4-(5-phenyl-1H-pyrrolo[2,3-b]pyridin-3-yl)benzoic acid, 2-(2-propyl)-4-(5-phenyl-1H-pyrrolo[2,3-b]pyridin-3-yl)benzoic acid, 6-(5-phenyl-1H-pyrrolo[2,3-b]pyridin-3-yl)-1H-indazole, 2-(2-methylpropyl)-4-(5-phenyl-1H-pyrrolo[2,3-b]pyridin-3-yl) benzoic acid, and 2-methyl-4-(5-phenyl-1H-pyrrolo[2,3-b]pyridin-3-yl)benzoic acid, and a pharmaceutically acceptable carrier, in an effective amount such that the symptoms of the melanoma in the subject are diminished.

\* \* \* \* \*

UNITED STATES PATENT AND TRADEMARK OFFICE
CERTIFICATE OF CORRECTION

| | |
|---|---|
| PATENT NO. | : 11,103,486 B2 |
| APPLICATION NO. | : 15/062576 |
| DATED | : August 31, 2021 |
| INVENTOR(S) | : Powell et al. |

It is certified that error appears in the above-identified patent and that said Letters Patent is hereby corrected as shown below:

In the Claims

Claim 4, Column 22, Line 5 reads:
"2-methylamino)-4-(5-phenyl-1H-pyrrolo[2,3-b]pyridin-3-"
Whereas it should read:
"2-(methylamino)-4-(5-phenyl-1H-pyrrolo[2,3-b]pyridin-3-"

Signed and Sealed this
Tenth Day of May, 2022

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 22
<212> TYPE: DNA
<213> ORGANISM: artificial sequence
<220> FEATURE:
<223> OTHER INFORMATION: synthetic sequence

<400> SEQUENCE: 1
ctcagtctct tttgggctct tt                                            22

<210> SEQ ID NO 2
<211> LENGTH: 22
<212> TYPE: DNA
<213> ORGANISM: artificial sequence
<220> FEATURE:
<223> OTHER INFORMATION: synthetic sequence

<400> SEQUENCE: 2
tttcttcttc aggatggctt tc                                            22
```